(12) United States Patent
Kurotaki et al.

(10) Patent No.: US 7,595,045 B2
(45) Date of Patent: Sep. 29, 2009

(54) ANTI-α9 INTEGRIN ANTIBODY AND THE USE THEREOF

(75) Inventors: Daisuke Kurotaki, Sapporo (JP);
Masashi Kanayama, Sapporo (JP);
Shigeyuki Kon, Sapporo (JP);
Toshimitsu Uede, Sapporo (JP)

(73) Assignee: Gene Techno Science Co., Ltd., Hokkaido (JP)

( * ) Notice: Subject to any disclaimer, the term of this patent is extended or adjusted under 35 U.S.C. 154(b) by 69 days.

(21) Appl. No.: 11/795,045

(22) PCT Filed: Jan. 12, 2006

(86) PCT No.: PCT/JP2006/300676
§ 371 (c)(1),
(2), (4) Date: Jul. 11, 2007

(87) PCT Pub. No.: WO2006/075784
PCT Pub. Date: Jul. 20, 2006

(65) Prior Publication Data
US 2008/0152653 A1 Jun. 26, 2008

(30) Foreign Application Priority Data
Jan. 13, 2005 (JP) .............................. 2005-006348

(51) Int. Cl.
*A61K 39/395* (2006.01)
*C07K 16/28* (2006.01)
(52) U.S. Cl. .............. 424/130.1; 424/143.1; 424/144.1; 530/388.22
(58) Field of Classification Search ........................ None
See application file for complete search history.

(56) References Cited
U.S. PATENT DOCUMENTS
2005/0272668 A1 * 12/2005 Yednock et al. ............... 514/19

OTHER PUBLICATIONS
Palmer et al. Sequence and tissue distribution of the integrin alpha 9 subunit, a novel partner of beta 1 that is widely distributed in epithelia and muscle. J Cell Biol. Dec. 1, 1993; 123(5): 1289-1297.*

Wang et al., "Differential regulation of airway epithelial integrins by growth factors," American Journal of Respiratory Cell and Molecular Biology, 1996, 15(5):664-672.

Strausberg et al., "Integrin alpha 9 [Mus musculus]", Online Oct. 27, 2004, NCBI Entrez Protein, Accession NP_598482 (retrieved on Feb. 16, 2006) from http://www.ncbi.nlm.nih.gov/entrez/viewer.fcgi?19526904:NCBI:7445434.

Taooka et al., "The integrin α9β1 mediates adhesion to activated endothelial cells and transdothelial neutrophil migration through interaction with vascular cell adhesion molecule-1," The Journal of Cell Biology, 1999, 145(2):413-420.

Smith et al., "Osteopontin N-terminal domain contains a cryptic adhesive sequence recognized by $α_9β_1$ integrin," The Journal of Biological Chemistry, 1996, 271(45):28485-91.

* cited by examiner

*Primary Examiner*—Maher M Haddad
(74) *Attorney, Agent, or Firm*—Foley & Lardner LLP

(57) ABSTRACT

The present invention provides an anti-mouse α9 integrin antibody, an anti-human α9 integrin antibody, a hybridoma producing any of the antibodies, a method of producing any of the antibodies and the hybridoma, and a pharmaceutical composition comprising any of the antibodies. The anti-α9 integrin antibody of the present invention inhibits the α9 integrin function thereby to exhibit therapeutic effects on cancer, e.g., the growth and metastasis of a cancer cell, and an inflammatory disease, e.g., rheumatoid arthritis, osteoarthritis, hepatitis, bronchial asthma, fibrosis, diabetes, arteriosclerosis, multiple sclerosis, granuloma, an inflammatory bowel disease (ulcerative colitis and Crohn's disease), an autoimmune disease and the like.

6 Claims, 23 Drawing Sheets

Fig. 3
Ventricle   choroid plexus
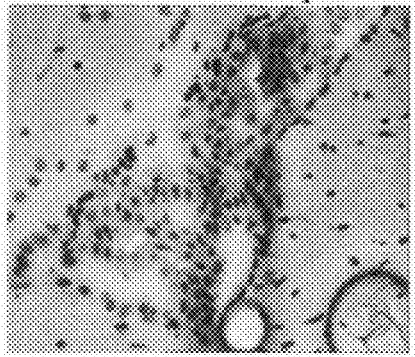 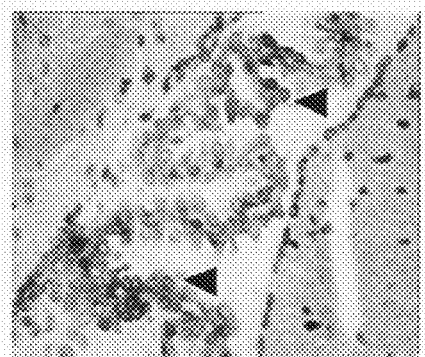
Liver   sinusoidal cell
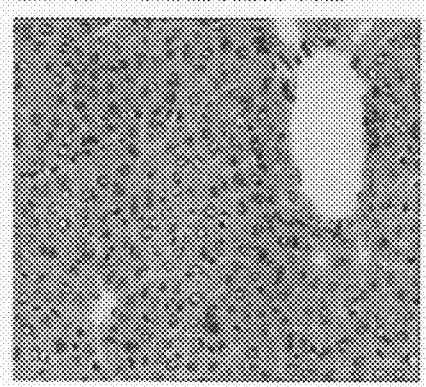 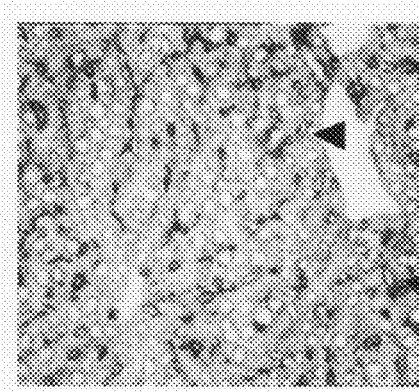
Alveoli   macrophage
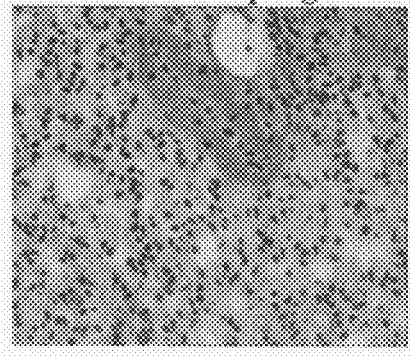 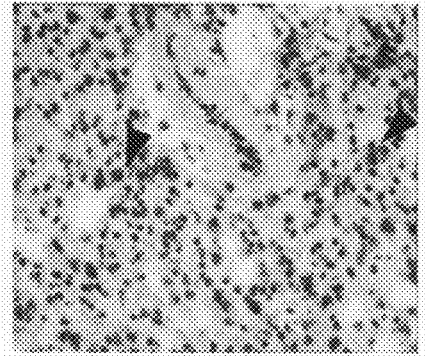
Muscle   myofibroblast
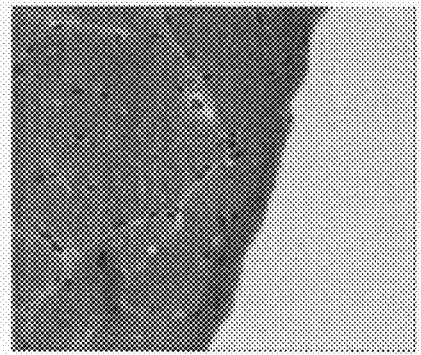 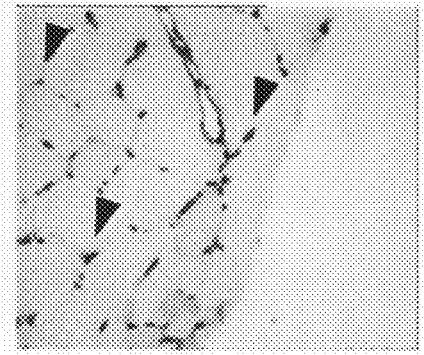

Fig. 4

| Tissue | α9 stainability |
|---|---|
| Brain | choroid plexus |
| Eyeball | — |
| Lung | +、vascular endothelium, • smooth muscle, • alveolar macrophage |
| Liver | +、sinusoidal cell |
| Heart | —、(vascular endothelium) |
| Kidney | +、vascular endothelium • smooth muscle • glomerulus |
| Stomach | +、smooth muscle • lamina muscularis mucosa |
| Muscle | +、vascular endothelium • myoblastoma, • lymphatic vessel |
| Uterus | +、vascular endothelium • smooth muscle • arterial smooth muscle |

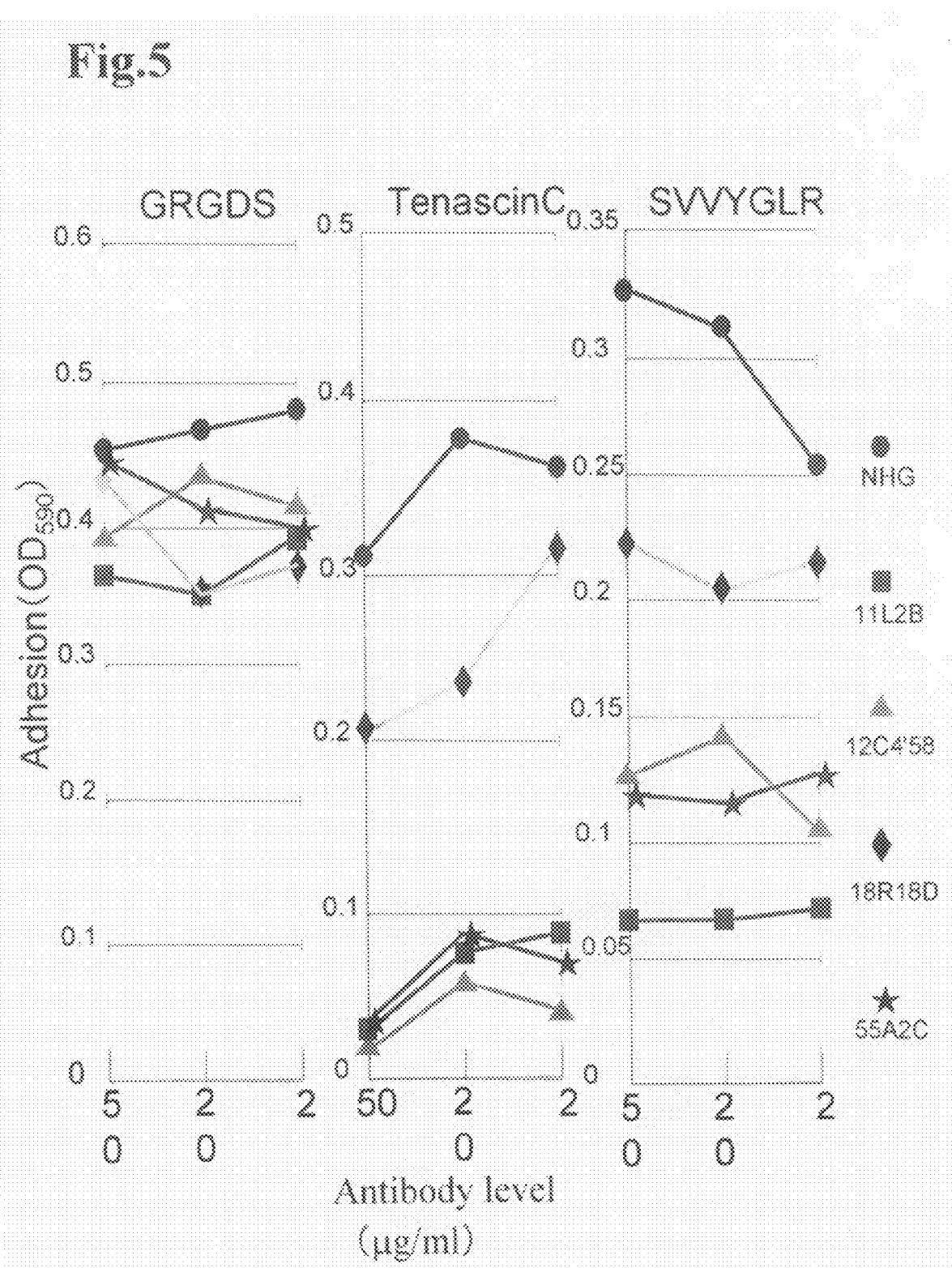

Fig.9
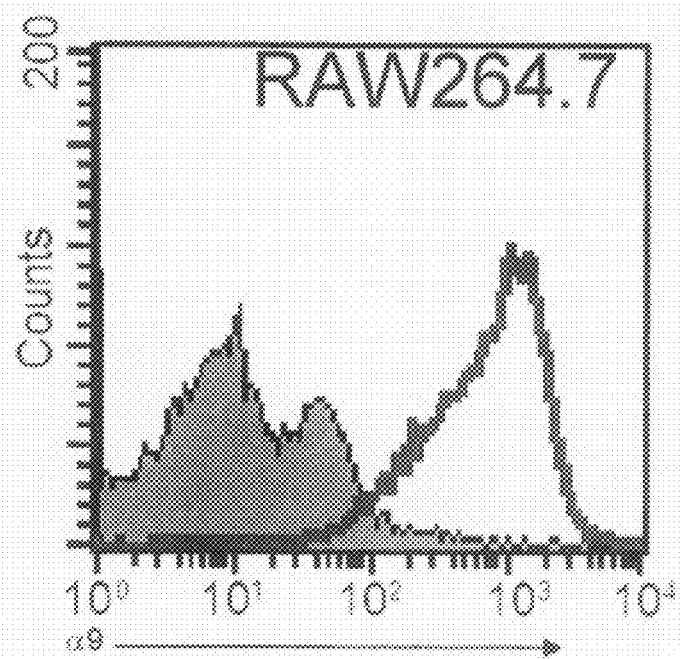
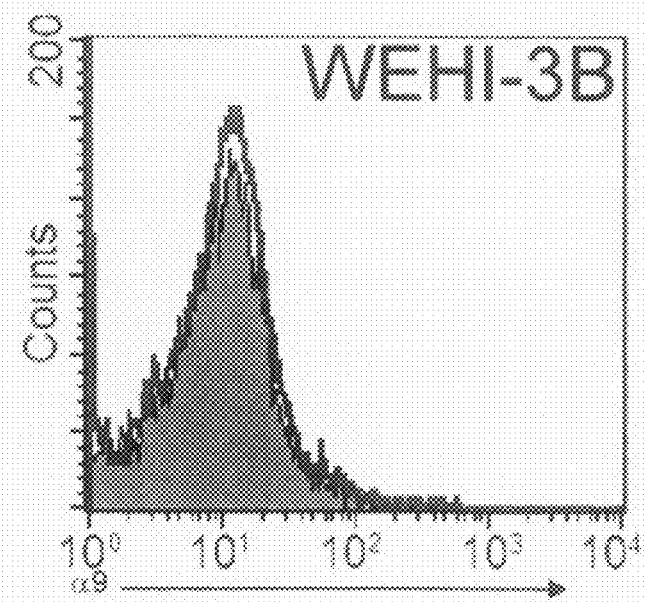

Fig. 11
A α9 Ab(-) α4 Ab(-)
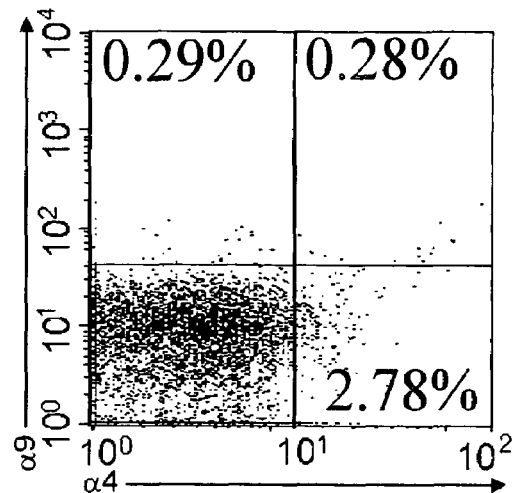
B α9 Ab(-) α4 Ab(+)
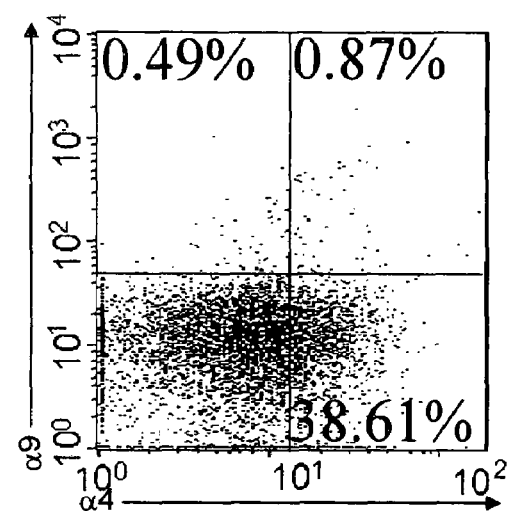
C α9 Ab(+) α4 Ab(+)
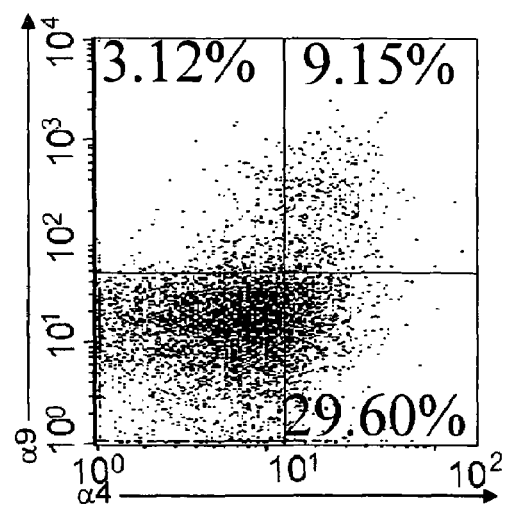

Fig. 12
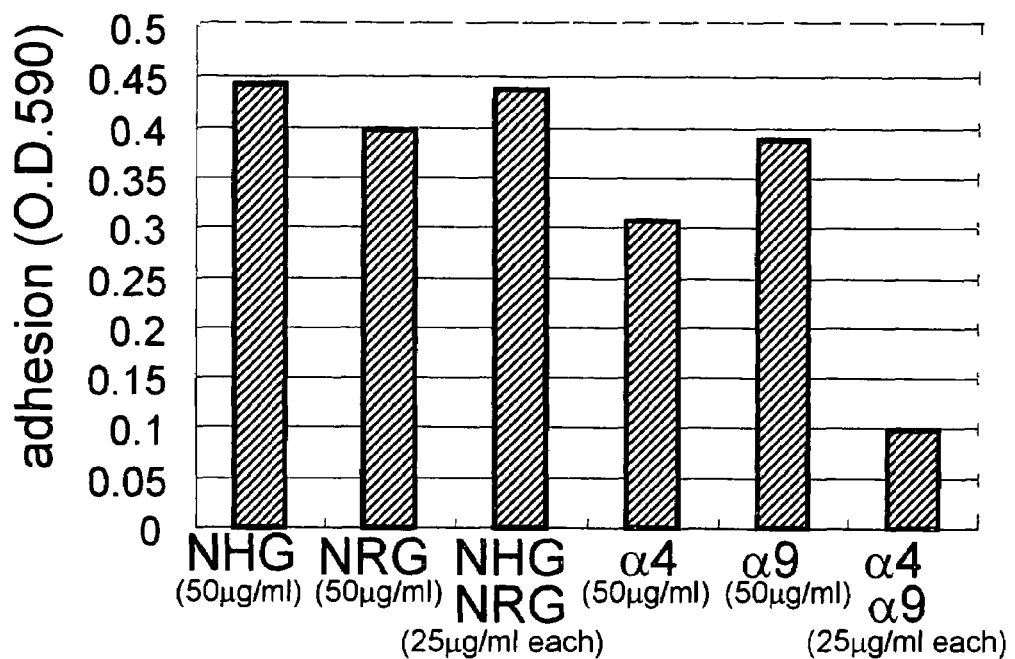
Run 1
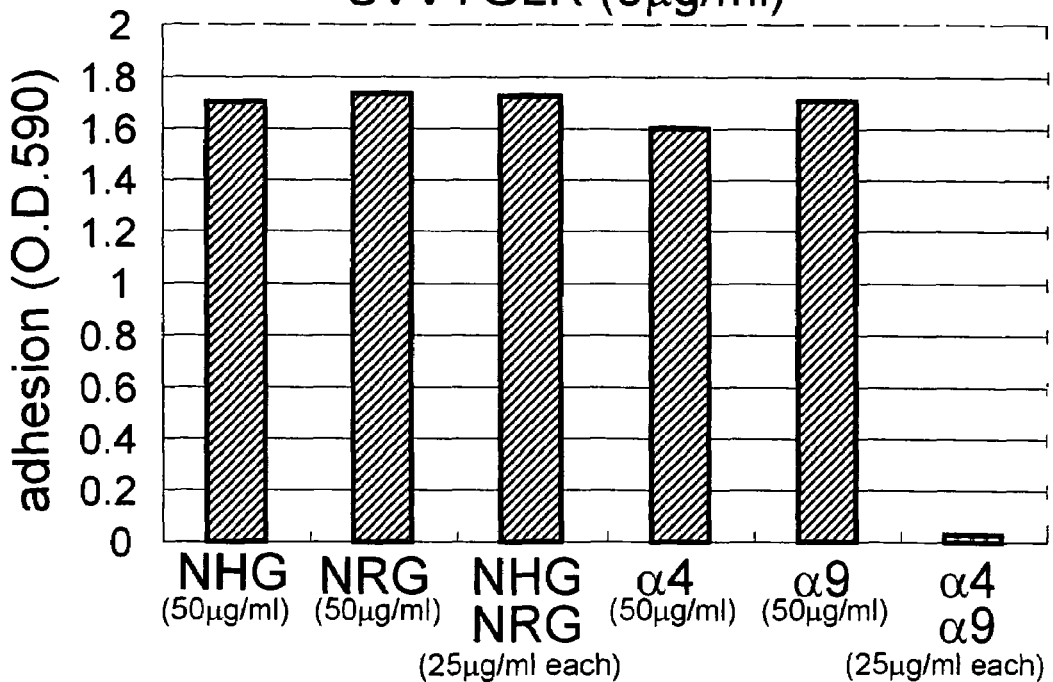
Run 2

Fig. 14
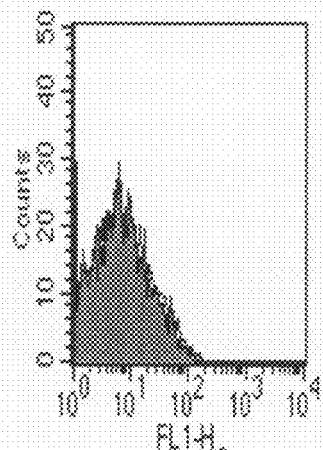
α4
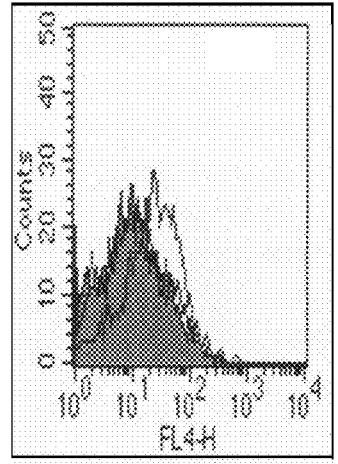
α9
phalloidin + DAPI   α9 + DAPI
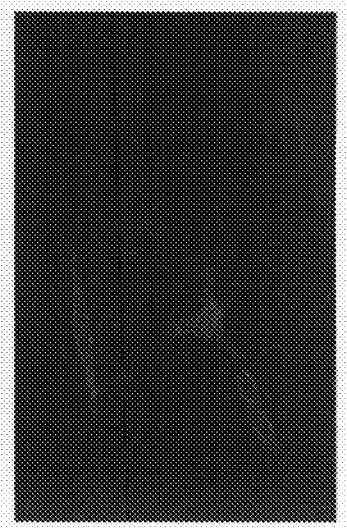

Neutrophils

Fig. 20
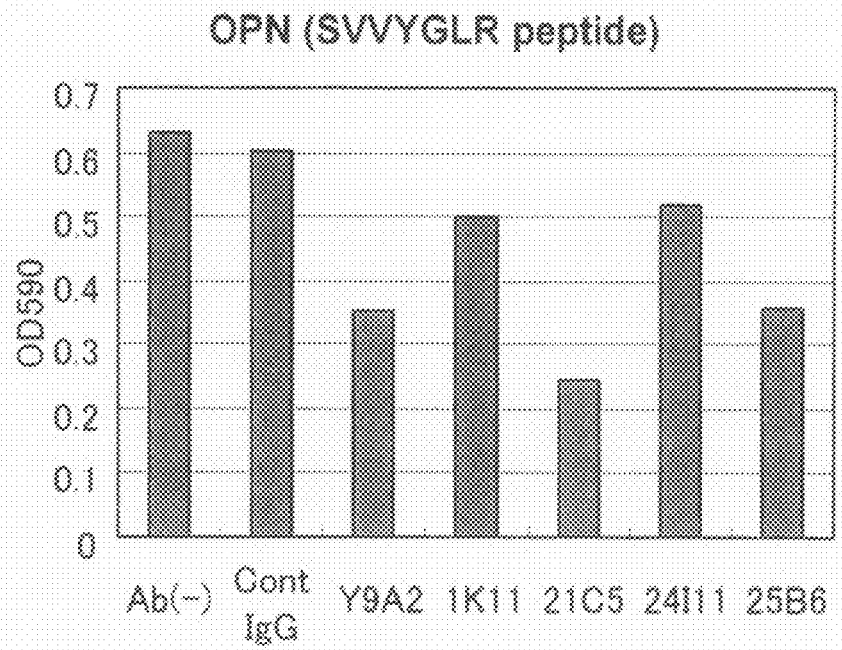
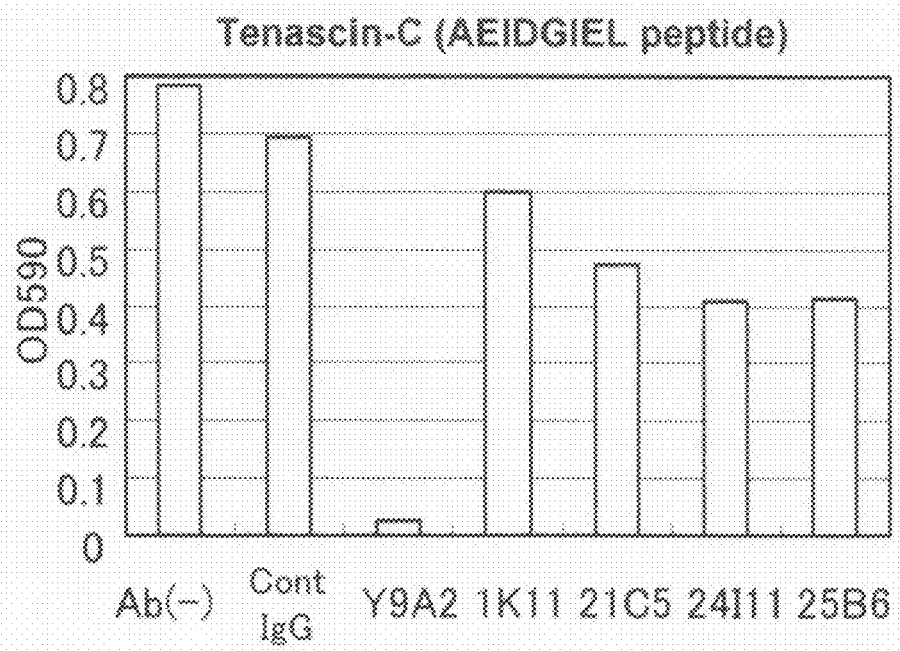

ANTI-α9 INTEGRIN ANTIBODY AND THE USE THEREOF

CROSS REFERENCE TO RELATED APPLICATIONS

This application is a National Stage application of PCT/JP2006/300676, filed Jan. 12, 2006, which claims priority from Japan patent application JP 005-006348, filed Jan. 13, 2005.

TECHNICAL FIELD

The present invention relates to monoclonal antibodies which specifically recognize human α9 integrin and mouse α9 integrin; hybridomas producing said monoclonal antibodies; pharmaceutical compositions comprising said monoclonal antibodies; diagnostic agents comprising said monoclonal antibodies; methods for producing said monoclonal antibodies; methods for producing said hybridomas; and so on.

BACKGROUND ART

Cells adhere to extracellular matrix (hereinafter abbreviated as ECM) mediated by a group of cell surface receptors which are termed integrins. Integrins perform their functions by forming 1:1 heterodimers of α and β chains. At least 18 types of α chain, 8 types of β chain and 24 types of αβ heterodimer have been identified and confirmed so far. It is known that each integrin recognizes a specific ligand. Integrins are classified into subfamilies depending upon the specificities or functions to ligands, and divided into collagen receptors, laminin receptors, RGD receptors recognizing an Arg-Gly-Asp (RGD) sequence present in fibronectin, vitronectin, etc., leukocyte-specific receptors present only in leukocytes (Non-Patent Literature 1: Hynes, R. O., 2002, Integrins: Bidirectional, Allosteric Signaling Machines. Cell 110: 673-87; Non-Patent Literature 2: Miyasaka, M., 2000, New edition of Adhesion Molecule Handbook, Shujunsya). The α4 and α9 integrins are a subfamily that does not belong to any of these types and called the α4 integrin subfamily (Non-Patent Literature 3: Elise L. Palmer, Curzio Rfiegg, Ronald Ferrando, Robert Pytela, Sheppard D., 1993, Sequence and Tissue Distribution of the Integrin α9 Subunit, a Novel Partner of β1 That Is Widely Distributed in Epithelia and Muscle. The Journal of Cell Biology, 123: 1289-97). On the other hand, ECM was considered so far to serve as a mere cementing substance between cells. It has now become clear that the integrin-mediated ECM-cell interaction is deeply involved in regulating the growth, adhesion, movement, etc. of cells and associated with the onset of diseases including a progression of cancer, an exacerbation of inflammation, etc.

Osteopontin (hereinafter abbreviated as OPN) which is one of ECM is a secreted, acidic phosphorylated glycoprotein with a molecular weight of about 41 kDa and is a molecule, which expression is widely observed in breast milk, urine, renal tubules, osteoclasts, osteoblasts, macrophages, activated T cells, tumor tissues, etc. OPN has the adhesion sequence GRGDS (SEQ ID NO: 16) at the center of its molecule, the SVVYGLR sequence (SEQ ID NO: 15) in human OPN or the SLAYGLR sequence (SEQ ID NO: 18) in mouse OPN and a thrombin-cleavage site in close proximity thereto, and binds through the GRGDS sequence (SEQ ID NO: 16) to the RGD integrin or to the α4 (α4β1) and α9 (α9β1) integrins through the SVVYGLR sequence (SEQ ID NO: 15) or the SLAYGLR sequence (SEQ ID NO: 18).

Differences in binding profile are also found in that α4β1 binds both to OPN not cleaved with thrombin (uncleaved OPN) and to the N-terminal fragment of thrombin-cleaved OPN (cleaved OPN), whereas α9β1 binds only to the cleaved OPN (Non-Patent Literature 4: Y. Yokosaki, et al., (1999) The Journal of Biological Chemistry, 274: 36328-36334; Non-Patent Literature 5: P. M. Green, et al., (2001) FEBS Letters, 503: 75-79; Non-Patent Literature 6: S. T. Barry, et al., (2000) Experimental Cell Research, 258: 342-351).

The α4 and α9 integrins share many common ligands other than OPN. Known ligands are the EDA domain of fibronectin, propeptide-von Willebrand factor (pp-vWF), tissue transglutaminase (tTG), blood coagulation factor XIII, vascular cell adhesion molecule-1(VCAM-1), etc. In addition, the CS-1 domain of fibronectin, MadCAM-1 (α4β7), etc. are known as the ligands specifically recognized by the α4 integrin. Tenascin-C, plasmin, etc. are known as the ligands specifically recognized by the α9 integrin.

The amino acid sequences for the integrin subunits α9, α4 and β1 are publicly known. For instance, human α9 is registered as NM_002207, mouse α9 as NM_133721, human α4 as NM_000885, mouse α4 as NM_010576, human β1 X07979, and mouse β1 as NM_010578, at the GenBank. These integrins are also known to have high similarities between species in amino acid sequence.

WO 02/081522 (Patent Literature 1) discloses a therapeutic effect on rheumatoid arthritis or hepatitis by inhibiting the OPN functions using OPN knockout mice or neutralizing antibodies against OPN. Moreover, this patent literature discloses that the SVVYGLR sequence (SEQ ID NO: 15) is essential as recognizing the α9 and α4 integrins for pathogenesis of an inflammatory disease and that receptors for OPN are expressed in immunocompetent cells or the like and associated with an inflammatory disease.

DISCLOSURE OF INVENTION

While a variety of drugs are known at present for the treatment of cancer, inflammatory diseases and autoimmune diseases, it has been desired to develop a preventive and/or therapeutic agent, etc. having more improved therapeutic effects on cancer, inflammatory diseases and autoimmune diseases.

Paying attention to the integrins, the present inventors have performed extensive studies and as a result, found that a specific inhibitory antibody against the α9 integrin has cancer-suppressing and anti-inflammatory effects. The present invention has thus been accomplished. Specifically, the present invention provides the monoclonal antibodies, hybridomas, pharmaceutical compositions, etc. described below.

(1) A monoclonal antibody, which specifically recognizes human α9 integrin and mouse α9 integrin.

(2) The monoclonal antibody according to (1) above, which inhibits the binding between human and/or mouse α9 integrin and a ligand of α9 integrin.

(3) The monoclonal antibody according to (2) above, wherein the ligand of α9 integrin is osteopontin.

(4) The monoclonal antibody according to any of (1) to (3) above, which is produced by a hybridoma designated by Accession No. FERM BP-10195, FERM BP-10196, FERM BP-10197 or FERM BP-10198.

(5) A hybridoma, which produces the monoclonal antibody according to any one of (1) to (4) above.

(6) A pharmaceutical composition comprising the monoclonal antibody according to any one of (1) to (4) above.

(7) A pharmaceutical composition comprising both the monoclonal antibody according to any one of (1) to (4) above and an anti-α4 integrin antibody.

(8) The pharmaceutical composition according to (6) or (7) above, which is an agent for preventing and/or treating inflammatory disease.

(9) A diagnostic agent for inflammatory disease, which comprises the monoclonal antibody according to any one of (1) to (4) above.

(10) A method for producing the monoclonal antibody according to any one of (1) to (4) above, which comprises using an α9 integrin-overexpressing cell as an antigen.

(11) A method for producing the hybridoma according to (5) above, which comprises using a different cell from the cell used as an antigen for overexpressing the α9 integrin.

(12) An inhibitor and/or promoter of cell and/or tissue remodeling, which comprises an α9 integrin-binding functional molecule (e.g., OPN, VCAM-1, tenascin-C, fibronectin, pp-vWF, tTG, etc.) as an active ingredient.

(13) A method for inhibiting and/or promoting cell and/or tissue remodeling, which comprises contacting an α9 integrin-expressing cell and/or tissue (e.g., tumor cells, leukocytes, smooth muscle, etc.) with an α9 integrin-binding functional molecule (e.g., OPN, VCAM-1, tenascin-C, fibronectin, pp-vWF, tTG, etc.).

The anti-α9 integrin antibody of the present invention inhibits the α9 integrin functions to exhibit therapeutic effects on cancer, e.g., the growth or metastasis of cancer cells, and an inflammatory disease, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, and the like.

Furthermore, the pharmaceutical composition comprising both the anti-α9 integrin antibody and the anti-α4 integrin antibody of the present invention exerts more improved therapeutic effects on an inflammatory disease. According to the present invention, the respective monoclonal antibodies against mouse α9 integrin and human α9 integrin are produced. The anti-mouse α9 integrin antibody can be used for animal tests and the anti-human α9 integrin antibody can be used as a therapeutic agent.

BRIEF DESCRIPTION OF THE DRAWINGS

FIG. 4 is a summary list of the results by immunostaining.

FIG. 5 shows cell adhesion inhibitory effects of 4 clones of the anti-mouse α9 integrin antibodies. 'GRGDS' disclosed as SEQ ID NO: 16. 'SVVYGLR' disclosed as SEQ ID NO: 15.

FIG. 9 shows the results of expression analysis of the α9 integrin in the monocytic cell line.

FIG. 11 shows the results of FACS analysis of liver infiltrating leukocytes from mice.

FIG. 12 shows the cell adhesion inhibitory effect of B16-BL6 by the anti-α4 integrin antibodies and α9-integrin antibodies. 'SVVYGLR' disclosed as SEQ ID NO: 15.

FIG. 14 shows the expression of α9 integrin in tendon fibroblasts.

FIG. 20 shows the cell adhesion inhibitory effects of the 4 clones of the anti-human α9 integrin antibodies and Y9A2. 'SVVYGLR' disclosed as SEQ ID NO: 15. 'AEIDGIEL' disclosed as SEQ ID NO: 17.

BEST MODE FOR CARRYING OUT THE INVENTION

Figure 1:
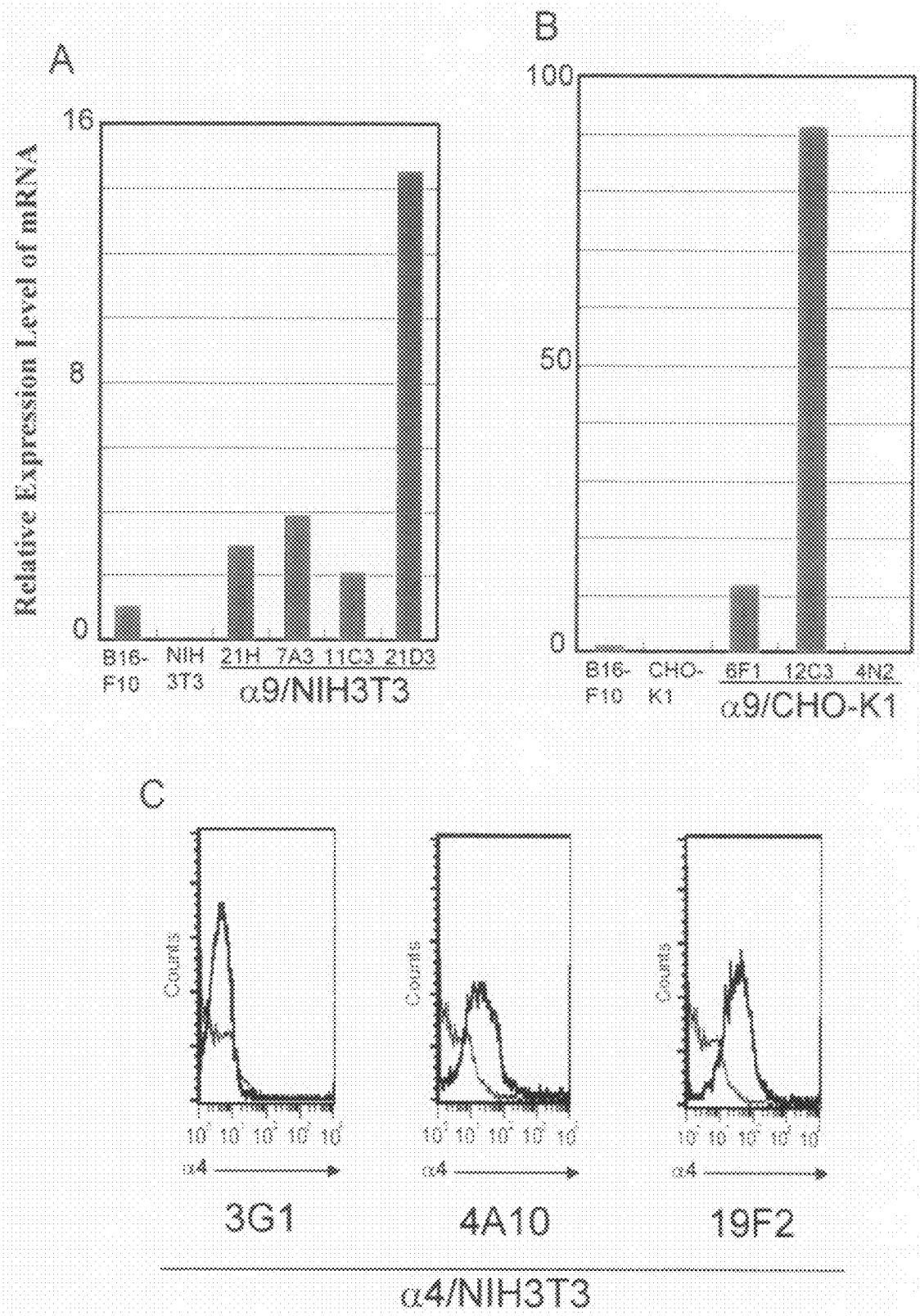
FIG. 1 shows the results of analysis of mRNA expression levels in the integrin gene-transfected cells.

Neutralizing antibodies against the α4 integrin as anti-integrin antibodies have already proceed to clinical trials. For instance, in July of 2004 the U.S. Food and Drug Administration (FDA) accepted a new drug application by Biogen Idec Inc. (Massachusetts, USA) and Elan Corporation (Ireland) for Tysabri (registered trademark) (natalizumab) as a drug for treating multiple sclerosis, and Tysabri (registered trademark) was designated as a drug for accelerated approval followed by priority review. Tysabri (registered trademark) is also targeted to treat Crohn's disease, rheumatoid arthritis, etc. The anti-human α4β1 integrin monoclonal antibody, which is termed P4C2, is also used for laboratory research.

However, antibodies against the α9 integrin are not clinically used, although a neutralizing antibody called Y9A2, whose antigen is human α9 integrin and which shows specificity to human and guinea pig α9 integrins, is used on a laboratory level (A. Wang et al., (1996) Am. J. Respir., Cell. Mol. Biol. 15, 664-672).

On the other hand, where anti-human α9 integrin antibodies are used as medicaments for human, the antibodies cannot be administered directly to human in the development process so that their effect cannot be confirmed. In other words, animal tests are required and if this effect can be confirmed, humanized antibodies or the like will be produced. Mice have characteristics in that their genetic background is clarified for most lines and their life-span per generation is short. It is also known that almost the same diseases as human diseases can be observed in mice, and mice are suitable as experimental animals. However, any neutralizing antibody showing the cross-reactivity with mouse α9 integrin has not been reported so far.

According to the present invention, the following four steps were carefully performed so that inhibitory antibodies specifically reacting with human and mouse α9 integrins, respectively, could be obtained.

(1) Production of α9 Integrin-overexpressing Cell Line

In general, screening of gene-expressing cells is performed on a protein level or gene level. Herein, the cells were screened for the cell adhesion ability, which is a function of the α9 integrin, to establish the cell line overexpressing human or mouse α9 integrin on the cell membrane.

The cells expressing human or mouse α9 integrin could be used in mice or hamsters for immunization.

(2) Cell Selection

Immunization of Syrian hamsters was considered to produce the antibodies against mouse α9 integrin. For that purpose, the gene of mouse α9 integrin was transfected into hamster ovary cells CHO-K1 to construct the experimental system in hamsters for increasing only the antibody titer of antibodies mainly against mouse α9 integrin.

For the antibodies against human α9 integrin, the gene of human α9 integrin was transfected into CHO-K1 cells to construct the experimental system in mice for increasing the antibodies against human α9 integrin.

(3) Screening of Hybridomas Producing Anti-mouse α9 Integrin Antibodies

To efficiently produce clones reacting only with mouse α9 integrin from various hybridomas, the α9 integrin-expressed cells (NIH3T3) different from the parent cells (CHO-K1) of the immunized ones were used for screening. Furthermore, the cells obtained by expressing mouse α4 integrin belonging to the same integrin family as the α9 integrin on the NIH3T3 cells were further used to screen clones showing no cross-reactivity with integrins other than the α9 integrin. Thus, the antibodies specifically reacting with mouse α9 integrin were efficiently produced.

(4) Screening of Hybridomas Producing Anti-human α9 Integrin Antibodies

To efficiently produce clones reacting only with human α9 integrin from various hybridomas, clones reacting with the gene-transfected CHO-K1 cells but not reacting with the CHO-K1 cells were screened. Further by confirming that the cells do not react with the human α4 integrin gene-transfected CHO-K1 cells, inhibitory antibodies specifically reacting with human α9 integrin were produced.

[Monoclonal Antibodies Against α9 Integrin]

The present invention provides monoclonal antibodies against the α9 integrin. As used herein, the term "antibody" is intended to mean an antibody molecule capable of binding to the α9 integrin, which is an antigen, as a whole or a fragment thereof (e.g., Fab or F(ab')$_2$ fragment). The antibody may be either polyclonal or monoclonal. Preferably, the antibody means a monoclonal antibody in the present invention. In the present invention, the term "antibody" includes a human antibody, a humanized antibody and a chimeric antibody.

The term "humanized antibody" described above refers to an antibody derived from non-human species such as mouse, etc., which is modified by replacing the primary structure other than the complementarity determining region in the H and L chains with the corresponding primary structure of a human antibody. The term "chimeric antibody" means an antibody having the Fab region and the Fc region that are derived from heteroantibodies.

As used in the present invention, the term "antibody fragment" refers to a portion of a full-length antibody, and generally refers to the antigen binding or variable region. The antibody fragment includes, for example, Fab, Fab', F(ab')$_2$ and Fv fragments. Papain digestion of antibodies produces two identical antigen binding fragments, called the Fab fragment, each with a single antigen binding site, and a residual "Fc" fragment called for its ability to crystallize readily. Furthermore, pepsin digestion gives an F(ab')$_2$ fragment that has two antigen binding sites which are capable of cross-linking antigens, and a residual other fragment (which is termed pFc').

As used herein, the term "Fv" fragment is the minimum antibody fragment that contains a complete antigen-recognition site and binding site. This region consists of a dimer ($V_H$-$V_L$ dimer) of one heavy chain and one light chain variable domain in a tight association via non-covalent binding. It is in such a configuration that the three CDRs of each variable domain interact to define an antigen-binding site on the surface of the $V_H$-$V_L$ dimer. The six CDRs confer antigen-binding specificity to the antibody. However, even a single variable domain (or a half of the Fv comprising only three CDRs specific for an antigen) has the ability to recognize and bind to the antigen, although it is at a lower affinity than in the entire binding sites.

The Fab fragment (which is also termed F(ab)) further contains the constant domain of the light chain and the constant domain of the heavy chain (CH1). Fab' fragments differ from Fab fragments by having a few additional residues derived from the carboxyl terminus of the heavy chain CH1 domain including one or more cysteines from the antibody hinge region.

The term "monoclonal antibody" as used in the present invention refers to an antibody obtained from a population of substantially homogeneous antibodies, namely, the individual antibodies which construct the population are homogeneous except for possible naturally occurring mutations that may be present in minor quantities. Monoclonal antibodies are highly specific and act against a single antigenic site. Furthermore, in contrast to polyclonal antibodies which include different antibodies against different epitopes, each monoclonal antibody is directed to a single epitope on the antigen. In addition to their specificity, the monoclonal antibodies are advantageous in that they are synthesized by the hybridoma culture which is uncontaminated by other immunoglobulins. The modifier "monoclonal" suggests the character of the antibody as being obtained from a substantially homogeneous population of antibodies, and is not to be so construed that the antibody should be produced by any particular method.

Hereinafter, production of the anti-α9 integrin monoclonal antibodies is described in detail but is not deemed to be limited thereto.

[α9 Integrin (Antigen)]

The α9 integrin used as an antigen in the present invention may be (1) proteins derived from all cells from human or other mammals that express α9 integrins, or all tissues where these cells are present, (2) recombinant proteins in which the α9 integrin-encoding gene DNA, preferably cDNA, is transfected into bacteria, yeast, cell lines including animal cells, etc. and expressed, or (3) synthetic proteins.

The α9 integrin of the present invention includes polypeptides comprising substantially the same amino acid sequences as the amino acid sequences of α9 integrins from various mammals, particularly preferably, the amino acid sequence of human α9 integrin (SEQ ID NO: 1).

Herein, the "polypeptides comprising substantially the same amino acid sequence" mean variant polypeptides comprising an amino acid sequence, in which multiple amino acids, preferably 1 to 10 amino acids and more preferably 1 to several (e.g., 1 to 5) amino acids are substituted, deleted and/or modified, as long as these variant polypeptides have biological properties substantially equivalent the naturally occurring α9 integrin, particularly preferably the human-derived α9 integrin; and variant polypeptides comprising an amino acid sequence, wherein multiple amino acids, preferably 1 to 10 amino acids and more preferably 1 to several (e.g., 1 to 5) amino acids are added to the amino acid sequence of naturally occurring α9 integrin, particularly preferably human-derived α9 integrin. Furthermore, the variant polypeptides may be those having a plurality of these substitutions, deletions, modifications and additions of amino acids.

The α9 integrin of the present invention, especially human-derived α9 integrin can be produced by appropriately using methods well known in the art, such as chemical synthesis method, cell culture method, etc., or their modifications, in addition to the gene recombinant techniques.

Examples of the methods for producing variant polypeptides include a synthetic oligonucleotide site-directed mutagenesis (gapped duplex method), a point mutagenesis method which involves introducing a point mutation at random by treatment with nitrite or sulfite, a method which involves preparing a deletion mutant with Bal31 enzyme, etc., a cassette mutagenesis, a linker scanning method, a miss incorporation method, a mismatch primer method, a DNA segment synthesis method, and the like.

The α9 integrin of the present invention also includes a "part" of said α9 integrin. As used herein, the "part" refers to a part comprising a region required for binding to a ligand of the α9 integrin, for example, OPN, VCAM-1, tenascin-C, etc., specifically, a part comprising the 14th-980th amino acid sequence represented by SEQ ID NO: 1, and a part comprising the 11th-981st amino acid sequence represented by SEQ ID NO: 2. The "part" of said α9 integrin can also be produced by gene recombination or chemical synthesis according to methods known in the art described below, or modifications thereof, or can be produced by appropriately digesting the α9 integrin isolated by the cell culture method, particularly preferably human-derived α9 integrin, with a proteolytic enzyme or the like.

As the antigen, a cell per se that overexpresses the α9 integrin on the cell membrane by recombinant technology, its membrane fraction or the like can be used.

The α9 integrin of the present invention also includes a polypeptide comprising substantially the same amino acid sequence as the amino acid sequence of human α9 integrin (SEQ ID NO: 1). Specifically, the polypeptide comprising substantially the same amino acid sequence as the amino acid sequence represented by SEQ ID NO: 1 includes mouse α9 integrin having the amino acid sequence represented by SEQ ID NO: 2. Since mice are considered as disease-model animals in the present invention, mouse-derived α9 integrin is preferably used as the antigen of the present invention. Especially in the present invention, a cell itself that overexpresses the α9 integrin on the cell membrane by recombinant technology or its cell membrane fraction is preferably employed. Accordingly, some polypeptides are prepared by cloning a gene (e.g., cDNA) encoding the α9 integrin by known genetic engineering techniques and using as the antigen the cell itself that overexpresses the α9 integrin on the cell membrane or its cell membrane fraction, as will be described below.

[Preparation of Antibody-producing Cell]

The antigen is administered to an animal to be immunized either solely or together with carriers or diluents to the site where the antibody can be produced by the administration. In order to potentiate the antibody productivity upon the administration, complete Freund's adjuvant or incomplete Freund's adjuvant may be administered. The administration is usually made once every about 1 to 6 weeks and about 2 to 10 times in total. Examples of warm-blooded animals used are mice, monkeys, rabbits, dogs, guinea pigs, rats, hamsters, sheep, goats, fowl, etc., with hamsters being preferably used in the present invention.

Where the subject to be treated is human and the OPN inhibitory antibody-producing animal is mouse, it is desired to use a human-mouse chimeric antibody or a humanized antibody. It is also desired to produce a human monoclonal antibody using a transgenic animal, e.g., a mouse, etc., into which a human gene associated with the antibody production is transfected, and use the produced monoclonal antibody.

[Cell Fusion of Antibody-producing Cells with Myeloma Cells]

As the myeloma cells, cells derived from mouse, rat, human, etc. are used. Examples include mouse myeloma P3U1, P3X63-Ag8, P3X63-Ag8-U1, P3NS1-Ag4, SP2/0-Ag14, P3X63-Ag8-653, etc. Preferably, the antibody-producing cells and myeloma cells are derived from allogeneic animals, especially from syngeneic animals. The myeloma cells can be stored frozen or maintained by subculture in a conventional medium supplemented with horse, rabbit or fetal calf serum. Preferably, cells at the exponential growth phase are used for the cell fusion. In the present invention, P3X63-Ag8-653 is advantageously used.

The method for fusing antibody-producing cells with myeloma cells to form hybridomas includes a method using polyethylene glycol (PEG), a method using Sendai virus, a method using an electrofusion device, etc. According to, e.g., the PEG method, the fusion is carried out as follows: spleen cells and myeloma cells are suspended in an appropriate medium or buffer containing about 30-60% PEG (average molecular weight of 1000 to 6000) at a mixing ratio of 1 to 10:1, preferably 5 to 10:1; the mixture is then reacted at a temperature of about 25 to 37° C. under pH conditions of 6 to 8 for about 30 seconds to about 3 minutes; after completion of the reaction, the PEG solution is removed and the cells are resuspended in a medium; and the suspension is inoculated on a cell-well plate followed by incubation.

[Screening of Hybridoma]

Screening of the monoclonal antibody-producing hybridomas can be performed by publicly known methods or their modifications. In general, screening can be performed in a medium for animal cells, to which HAT (hypoxanthine, aminopterin and thymidine) is added. Any medium may be used as a selection and growth medium, so long as the hybridomas can grow therein. For example, an RPMI 1640 medium containing 1 to 20%, preferably 10 to 20% fetal calf serum, a GIT medium containing 1 to 10% fetal calf serum (Wako Pure Chemical Industries, Ltd.), a serum-free medium for hybridoma culture (SFM-101, Nissui Pharmaceutical Co., Ltd.), or the like can be used. Incubation temperature is generally 20 to 40° C., and preferably about 37° C. Incubation time is generally 5 days to 3 weeks, and preferably 1 to 2 weeks. Incubation can be carried out generally under 5% carbon dioxide gas.

Production of the monoclonal antibodies of the present invention can be confirmed and screened by the cell ELISA assay, which is described in SHIN-RINSHO MEN-EKI JIKKEN SOSAHO (New Experimental Clinical Immunology) (part 3), Kagaku Hyoronsha, 1997. Where it is expected that when the cells used for immunization are used for screening, the background will increase or false positive results will often be given, clones reacting with the α9 integrin overexpressed in the other cells than the cells used for immunization and not reacting with cells overexpressing the α4 integrin can be used as the anti-α9 integrin antibodies. The monoclonal antibodies can be produced from such clones by applying the limiting dilution 1 to 5 times, preferably by repeating the limiting dilution 2 to 4 times.

[Separation And Purification of Antibody]

The antibodies produced can be purified to homogeneity. Any standard method for protein separation and purification can be used for separation and purification of the antibodies. For example, column chromatography such as affinity chromatography, etc., filtration, ultrafiltration, salting-out, dialysis, SDS polyacrylamide gel electrophoresis, isoelectric point electrophoresis, etc. may be appropriately combined to isolate and purify the antibodies (Antibodies: A Laboratory Manual. Ed Harlow and David Lane, Cold Spring Harbor Laboratory, 1988), but they are not limited thereto. The column used for affinity chromatography includes Protein A column and Protein G column. Examples of the column using Protein A column are Hyper D, POROS, Sepharose F. F. (Amersham Biosciences) and the like.

[Labeling of Antibody]

The antibodies obtained can be labeled in various ways using a known method or commercially available kit (e.g., biotin labeling, FITC labeling, APC labeling). According to the present invention, biotin labeling using Biotin Labeling Kit (Dojin Kagaku) is advantageously used.

[Pharmaceutical Composition Comprising the Monoclonal Antibody of the Invention]

The present invention provides the pharmaceutical composition comprising the monoclonal antibody described above. The pharmaceutical composition comprising the monoclonal antibody of the present invention as an active ingredient can be used as an agent for preventing and/or treating cancer, e.g., the growth or metastasis of cancer cells, and an inflammatory disease, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, and the like.

The pharmaceutical composition comprising the monoclonal antibody of the present invention can also be used to treat chronic rejection after organ transplantation, and an autoimmune disease such as systemic autoimmune disease, erythematosus, uveitis, Behcet's disease, polymyositis, glomerular proliferative nephritis, sarcoidosis, etc.

The preventive and/or therapeutic agent for treating the diseases described above, which comprises the antibody of the present invention, is low toxic and can be administered to human or mammals (e.g., rats, rabbits, sheep, swine, bovine, cats, dogs, monkeys, etc.) orally or parenterally, directly as a liquid preparation by mixing in a suitable solvent, or as a pharmaceutical composition in an appropriate dosage form. The dose may vary depending upon subject to be administered, target disease, conditions, route of administration, etc. When the antibody is used for preventing and/or treating an adult patient with, e.g., rheumatoid arthritis, it is advantageous to intravenously administer the antibody of the present invention normally at a single dose of about 0.01 to about 20 mg/kg body weight, preferably about 0.1 to about 10 mg/kg body weight, and more preferably about 0.1 to about 5 mg/kg body weight, approximately 1 to 5 times. per day, preferably approximately 1 to 3 times per day. In other parenteral administration and oral administration, the antibody can be administered in a dose corresponding to the dose given above. When the condition is especially severe, the dose may be increased according to the condition.

The antibody of the present invention can be administered directly as it stands or as an appropriate pharmaceutical composition. The pharmaceutical composition used for the administration described above contains the aforesaid antibody or salts thereof and pharmacologically acceptable carriers, diluents or excipients. Such a composition is provided in a dosage form suitable for oral or parenteral administration.

That is, examples of the composition for oral administration include solid or liquid dosage forms, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, etc. The injectable preparations may include dosage forms such as intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage form in a unit dose; especially in the form of injection, it is preferred that the aforesaid antibody is contained in about 5 to 100 mg and in about 10 to 250 mg for the other dosage forms.

Each composition described above may further contain other active components unless formulation causes any adverse interaction with the antibodies described above.

The present invention also related to an inhibitor and/or promoter for cell and/or tissue remodeling, which comprises an α9 integrin-binding functional molecule (e.g., OPN, VCAM-1, tenascin-C, fibronectin, pp-vWF, tTG, etc.) as an active ingredient; and a method for inhibiting and/or promoting cell and/or tissue remodeling, which comprises contacting the α9 integrin-expressing cell and/or tissue (e.g., a tumor cell, neutrophil, smooth muscle, etc.) with the α9 integrin-binding functional molecule. The dose, method for administration, pharmaceutical preparation, etc. of the active ingredient in such a therapeutic agent can be appropriately determined by referring to the foregoing description of medicaments comprising the antibodies.

[Diagnostic Agent Comprising the Monoclonal Antibody of the Invention]

The pharmaceutical composition comprising the monoclonal antibody of the present invention can be used as a diagnostic agent for cancer, e.g., the growth or metastasis of cancer cells, and an inflammatory disease, e.g., rheumatoid arthritis, osteoarthritis, hepatitis, bronchial asthma, fibrosis, diabetes mellitus, cancer metastasis, arteriosclerosis, multiple sclerosis, granuloma, etc., or as a diagnostic agent for chronic rejection after organ transplantation, an autoimmune disease such as systemic autoimmune disease, erythematosus, uveitis, Behcet's disease, polymyositis, glomerular proliferative nephritis, sarcoidosis, etc. The monoclonal antibodies of the present invention are capable of specifically recognizing the α9 integrin and hence can be used to quantify the α9 integrin in a test fluid, especially for quantification by the sandwich immunoassay, competitive assay, immunometry, nephrometry, etc., immunostaining, or the like. In applying these immunological methods to the assay methods of the present invention, it is not required to set forth any particular conditions, procedures, etc. It is sufficient to construct assay systems by adding ordinary technical consideration in the art to conventional conditions and procedures. For details of these general technical means, reference can be made to reviews, texts or the like.

As described above, the α9 integrin can be quantified with high sensitivity by using the antibodies of the present invention. Furthermore, various diseases associated with the α9 integrin can be diagnosed by applying the method for quantifying the α9 integrin in vivo. For instance, where an increase or decrease in the expression level of the α9 integrin is detected, it can be diagnosed that it is highly likely that one now suffers from diseases associated with the α9 integrin, e.g., cancer or an inflammatory disease, or it is highly likely that one will suffer from these diseases in the future. The monoclonal antibodies of the present invention can also be used for specifically detecting the α9 integrin present in a test fluid such as a body fluid, a tissue, etc. The monoclonal antibodies can also be used for preparation of antibody columns for purification of the α9 integrin, for detection of the α9 integrin contained in each fraction upon purification or for analysis of behaviors of the α9 integrin in cells to be tested.

EXAMPLES

Hereinafter, the present invention will be described in more detail but is not deemed to be limited thereto.

Example 1

[Cloning of Mouse α9, α4 Integrin cDNAs]

The α4 integrin gene and α9 integrin were reverse-transcribed from mouse 12.5-day embryos and the total RNA of B16-BL6 cells (mouse melanoma cells), respectively, using random primers. Cloning was carried out using the resulting cDNAs as templates. The primers used for the cloning are shown below.

```
mα4 Integin-5':
                                    (SEQ ID NO: 3)
5'-CGTGGATCCGAGCGCATGGCTGCGGAAGCGAGGTGC-3' mα4 Integin-3':
                                    (SEQ ID NO: 4)
5'-CAGCTCGAGTCAGTCATCATTGCTTTTGCTGTTGAC-3'
```

```
-continued
mα9 Integin-5':
                                    (SEQ ID NO: 5)
5'-GTCAAGCTTCTGGGGATGGGCGGCCCGGCTGGGCTG-3' mα9 Integin-3':
                                    (SEQ ID NO: 6)
5'-CGGTCTAGACACGGTGGGTCACTGGTTTTTCTGGAC-3'
```

PCR was carried out in the reaction system of 5 μl of cDNA as a template, 25 μl of GC buffer I, 5 μl of dNTPmix, 1 μl of 10 μM primer 1, 1 μl of 10 μM primer 2, 10.5 μl of DW and 0.5 μl of LA Taq (TaKaRa LA Taq (registered trademark)) under the reaction conditions: 94° C. for 2 minutes→(94° C. for 30 seconds→68° C. for 3 minutes, 30 cycles)→4° C. in a thermal cycler (GerieAmp (registered trademark) PCR System 2700 (Applied Biosystems)). After the reaction, the band around 3 kb for α4 integrin and the band around 3 kb for α9 integrin were separated by 1% agarose gel electrophoresis and then excised from the gel. The PCR amplification product was purified using QIAquick (registered trademark) Gel Extraction Kit (QIAGEN).

[Cloning of Human α9, α4 Integrin cDNAs]

The α4 integrin gene and α9 integrin were reverse-transcribed from the total RNA extracted from human neutrophils and human peripheral mononuclear cells, respectively, using random primers. Using the obtained cDNAs as templates, cloning was performed by PCR. The primers used for the cloning are shown below.

```
hα4 Integin-5':
                                    (SEQ ID NO: 11)
5'-ACGCTCGAGTGTACCATGTTCCCCACCGAGAGCGCA-3' hα4 Integin-3':
                                    (SEQ ID NO: 12)
5'-TCATCTAGATTAATCATCATTGCTTTTACT-3' hα9 Integin-5':
                                    (SEQ ID NO: 13)
5'-TCGAAGCTTCTGGGGATGGGCGGCCCGGCT-3' hα9 Integin-3':
                                    (SEQ ID NO: 14)
5'-ACCTCTAGATCACTGGTTTTTCTGGACCCA-3'
```

As described above, the respective cDNAs of the α4 and α9 integrins amplified by PCR were incorporated into pCRII-TOPO (registered trademark) vector (Invitrogen) and the respective base sequences were confirmed by ABI PRISM (registered trademark) 310 (Applied Biosystems). The base sequences of cDNAs obtained coincided with SEQ ID NO: 7 (mouse α9) and SEQ ID NO: 8 (mouse α4), and SEQ ID NO: 9 (human α9) and SEQ ID NO: 10 (human α4), respectively. To transfect these cDNAs into animal cells, they were incorporated into pcDNA™ 3.1(+)(Invitrogen). The thus obtained vectors were named mouse α9 integrin/pcDNA3.1, mouse α4 integrin/pcDNA3.1, human α9 integrin/pcDNA3.1 and human α4 integrin/pcDNA3.1, respectively.

Example 2

[Establishment of Cell Lines Stably Expressing α9 And α4 Integrins]

To immunize hamsters, mouse α4 integrin/pcDNA3.1 carrying α4 integrin or α9 integrin/pcDNA3.1 carrying mouse α9 integrin was transfected into a hamster ovary cell line, CHO-K1 cells. By screening for the ability of adhering to the SVVYGLR peptide (SEQ ID NO: 15) of OPN, three clones (6F1, 12C3 and 4N2) of the CHO-K1 cells (mouse α9/CHO-K1 cells) and four clones (21H, 7A3, 11C3 and 21D3) of the NIH3T3 cells (mouse α9/NIH3T3 cells), which stably expressed the mouse α9 integrin, were established.

As control for the mouse α9 integrin, the α4 integrin belonging to the same integrin subfamily was cloned from mouse 12.5-day embryos, and three clones (3G1, 4A10 and 19F2) of the NIH3T3 cells (mouse α4/NIH3T3 cells) stably expressing the mouse α4 integrin were established.

For quantitative analysis of the α9 integrin expression level in the established mouse α9 integrin-expressing cells, real-time PCR was carried out using cDNAs extracted from the α9/NIH3T3 cells and α9/CHO-K1 cells. As shown in FIG. 1A and FIG. 1B, the highest expression of α9 integrin was noted with 21D3 in the α9/NIH3T3 cells and with 12C3 in the α9/CHO-K1 cells. In the α4/NIH3T3 cells, the protein expression level was analyzed by FACS and the results are shown in FIG. 1C. The maximum increase of mouse α4 integrin expression was observed with 4A10.

In a similar manner, one clone (20J1) of the CHO-K1 cells (human α9/CHO-K1 cells) stably expressing human α9 integrin and one clone (9A5) of the CHO-K1 cells (human α4/CHO-K1 cells) stably expressing human α4 integrin were established.

Example 3

[FACS Analysis Using Anti-α9 Integrin Antibodies]

Using the mouse α9/CHO-K1 cells per se as an antigen, three Syrian hamsters (7-8 weeks old, female) were immunized 5 times in total at $1 \times 10^7$ cells/time/animal. Spleen cells were isolated and fused with mouse myeloma cells or X63-Ag8-653 by the PEG method, and hybridomas were selected in HAT medium. The monoclonal antibodies were produced by screening using cell ELISA. Since it was expected that when the cells used for immunization were used for screening, the background would increase or false positive results would often be given, clones which reacted with the mouse α9/NIH3T3 cells but did not react with the mouse α4/NIH3T3 cells were made the anti-α9 integrin antibodies. The monoclonal antibodies were established by repeating the limiting dilution twice. As a result, the four anti-mouse α9 integrin antibody-producing hybridoma clones (11L2B, 12C4'58, 18R18D and 55A2C) were established.

In producing the antibodies against the human α9 integrin, three BALB/c mice were immunized, based on the subtractive immunization technique (Williams, C. V., Stechmann, C. L., McLoon, S. C., Biotechniques (1992) 12: 842-7). First, CHO-K1 cells were intraperitoneally injected at $4 \times 10^6$/animal, and cyclophosphamide was intraperitoneally injected at 4 mg/animal on the following day and further on the following day. Two weeks after the cyclophosphamide injection, human α9/CHO-K1 cells were intraperitoneally injected at $2 \times 10^6$/animal and further 2 weeks after, the human α9/CHO-K1 cells were intraperitoneally injected at $3 \times 10^6$/animal. Clones that reacted with the human α9/CHO-K1 cells but did not react with the human α4/CHO-K1 cells were made as the anti-α9 integrin antibodies. As a result, the four anti-human α9 integrin antibody-producing hybridoma clones (1K11, 21C5, 24I11 and 25B6) were established.

Hybridoma 11L2B producing the anti-mouse α9 integrin antibody obtained herein has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-10197 since Dec. 28, 2004.

Hybridoma 12C4'58 obtained herein has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-10196 since Dec. 28, 2004.

Hybridoma 18R18D obtained herein has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-10195 since Dec. 28, 2004.

Hybridoma 55A2C obtained herein has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-10198 since Dec. 28, 2004.

Whether the anti-mouse α9 integrin antibodies were usable for FACS was examined using the mouse α9 NIH3T3 cells and mouse α4/NIH3T3 cells. All runs were performed at the cell count of $1.0 \times 10^5$ and the antibodies were reacted on ice. To block any non-specific reaction with the Fc receptor, anti-FcγRII antibody (2.4G2) was added and then a primary antibody was added. To the 2.4G2-treated α9/NIH3T3 cells or α4/NIH3T3 cells, or the mouse melanoma cell line, B16-BL6 cells expressing the endogenous α9 integrin, the produced antibody (5 μg/ml) was added as a primary antibody, followed by reacting them for 30 minutes. Next, 50 μl of FITC-labeled anti-hamster IgG antibody was added thereto. After reacting them for 30 minutes, the mixture was passed through a nylon mesh and analyzed by FACS using FACSCalibur™ (Becton Dickinson). In using biotinylated antibodies, 50 μl of the biotinylated antibody (5 μg/ml) was added to the 2.4G2-treated cells to block the Fc receptor. After reacting them for 30 minutes, 50 μl of APC-labeled or FITC-labeled streptoavidin was added thereto, which was provided for the FACS analysis.

Figures 1, 2:
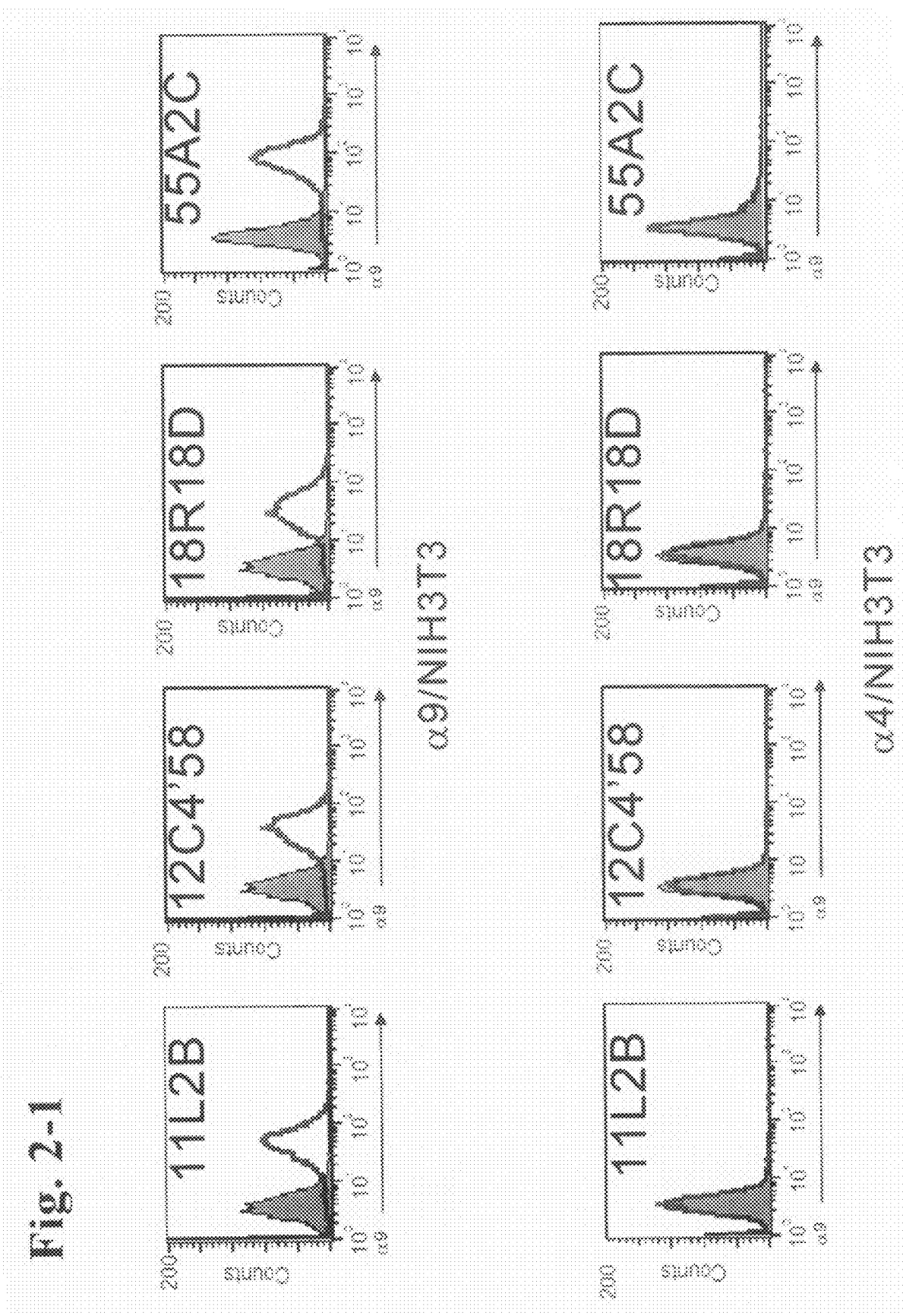
FIG. 2 shows the results of analysis of the anti-mouse α9 integrin antibodies by FACS.
Figure 2:
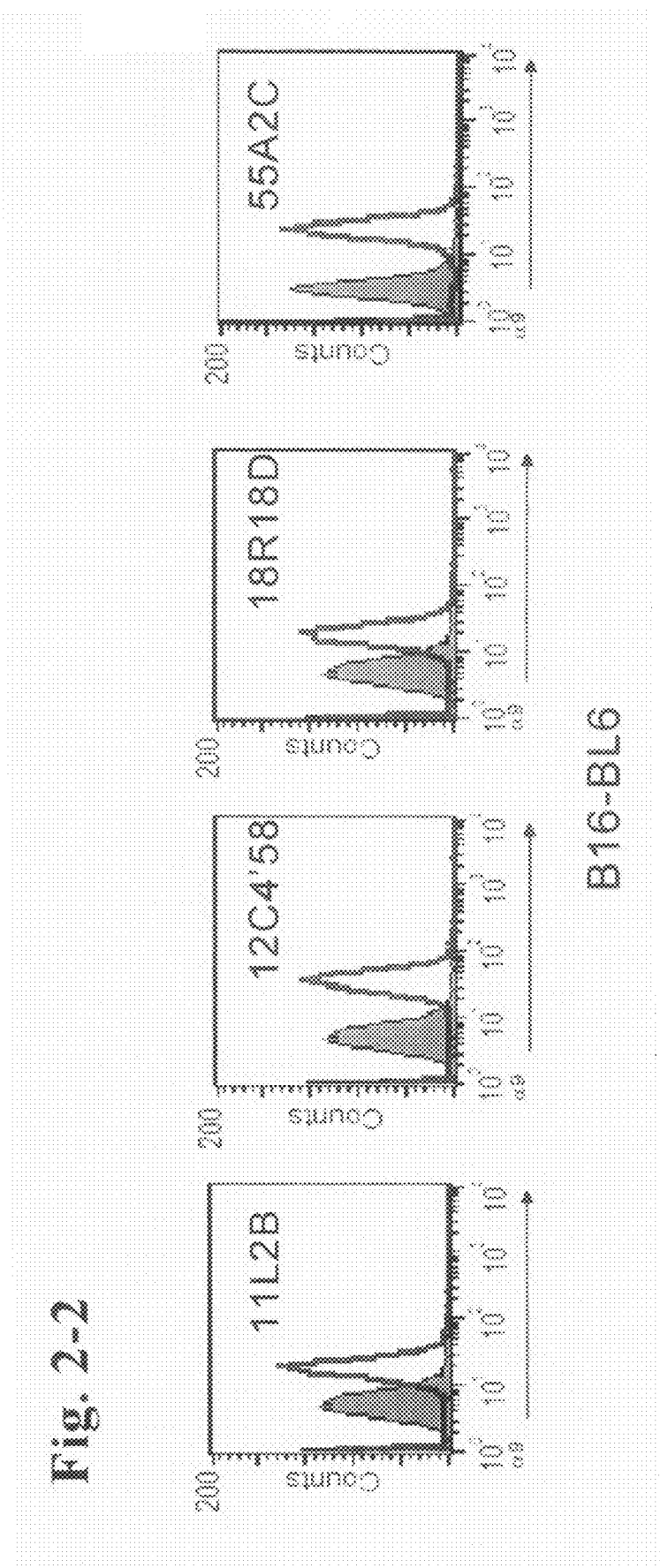

As a result, the α9 integrin on the mouse α9/NIH3T3 cells and B16-BL6 cells could be detected by the anti-mouse α9 integrin antibodies, as shown in FIG. 2. Any antibody did not react with the mouse α4/NIH3T3 cells. These results reveal that all of the anti-mouse α9 integrin antibodies can detect the mouse α9 integrin protein expressed on cells by FACS.

Example 4

[Analysis of Cell Staining]

Figures 1, 19:
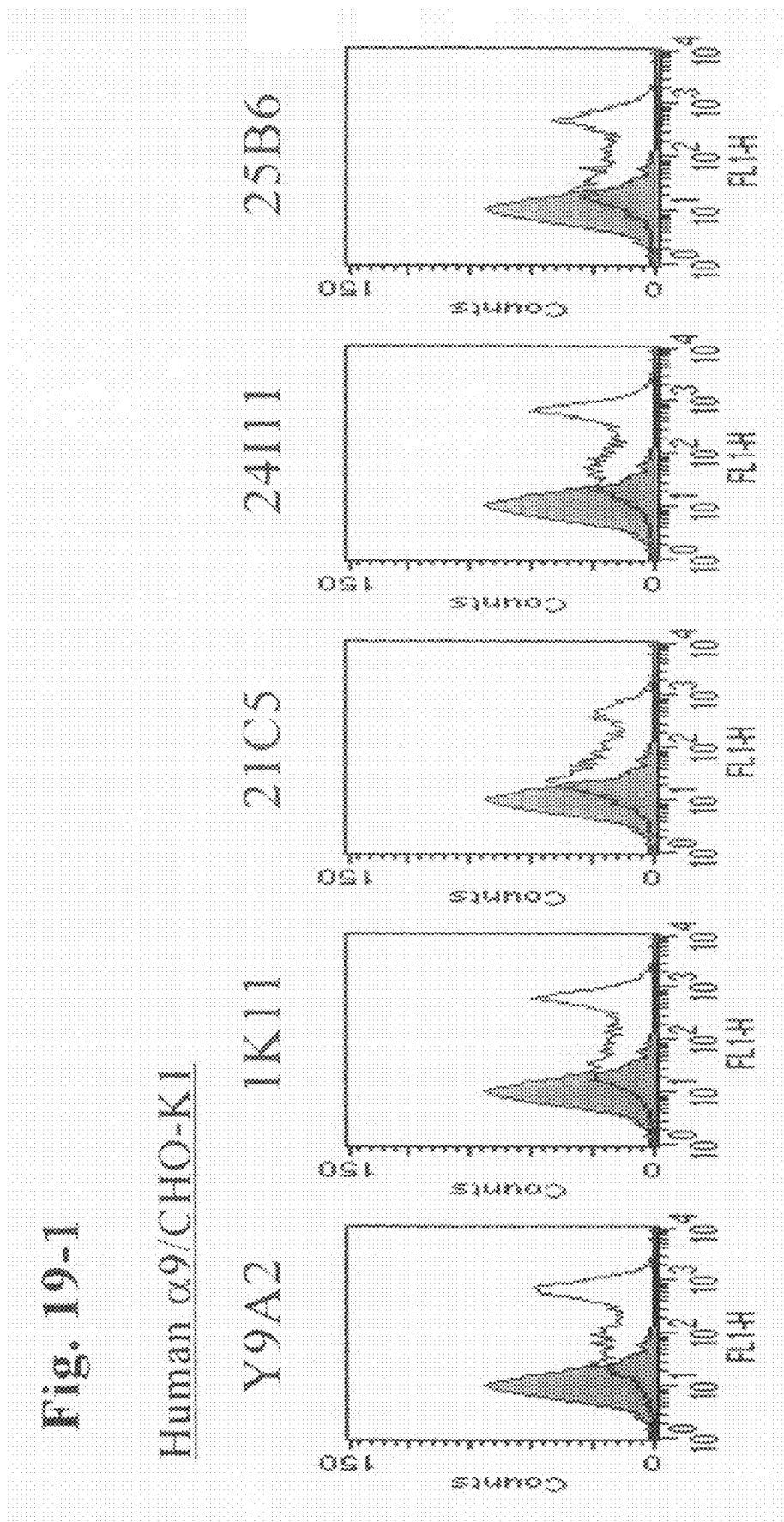
FIG. 19 shows the results of FACS analysis of the anti-human α9 integrin antibodies.
Figures 2, 19:
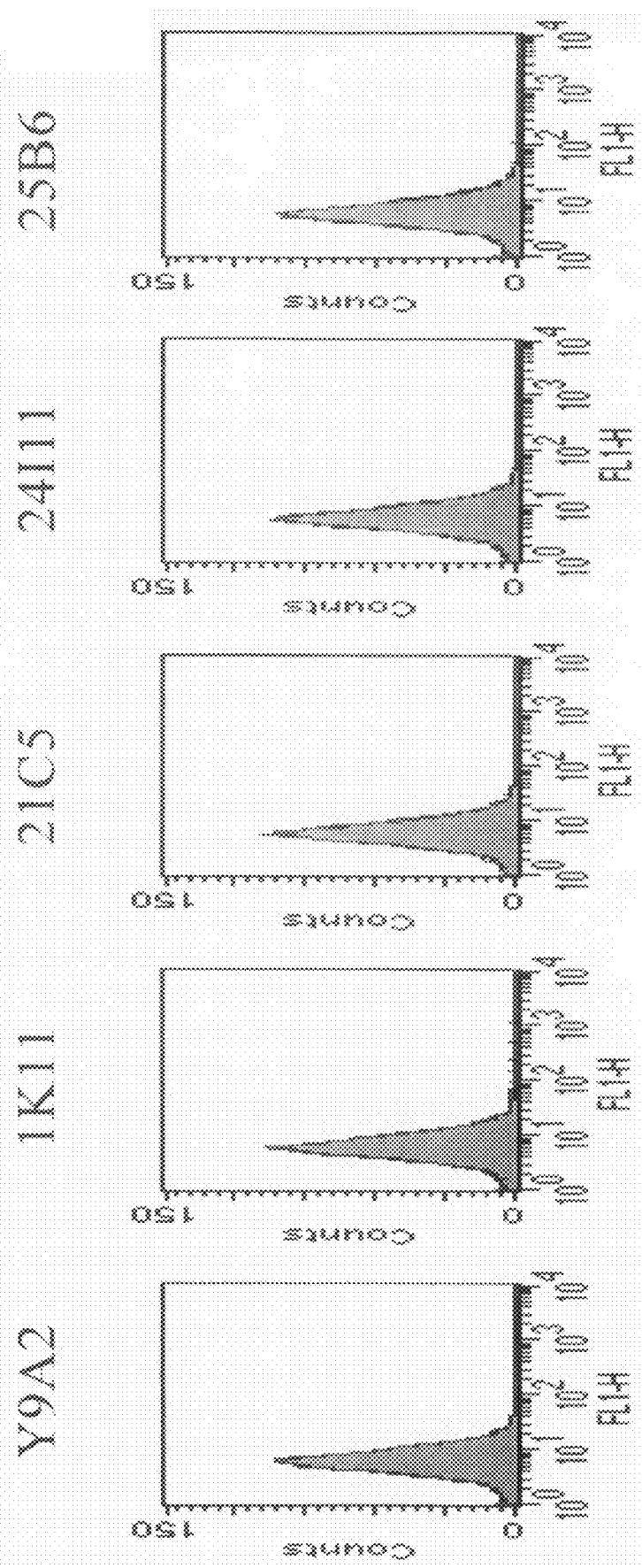
Figures 3, 19:
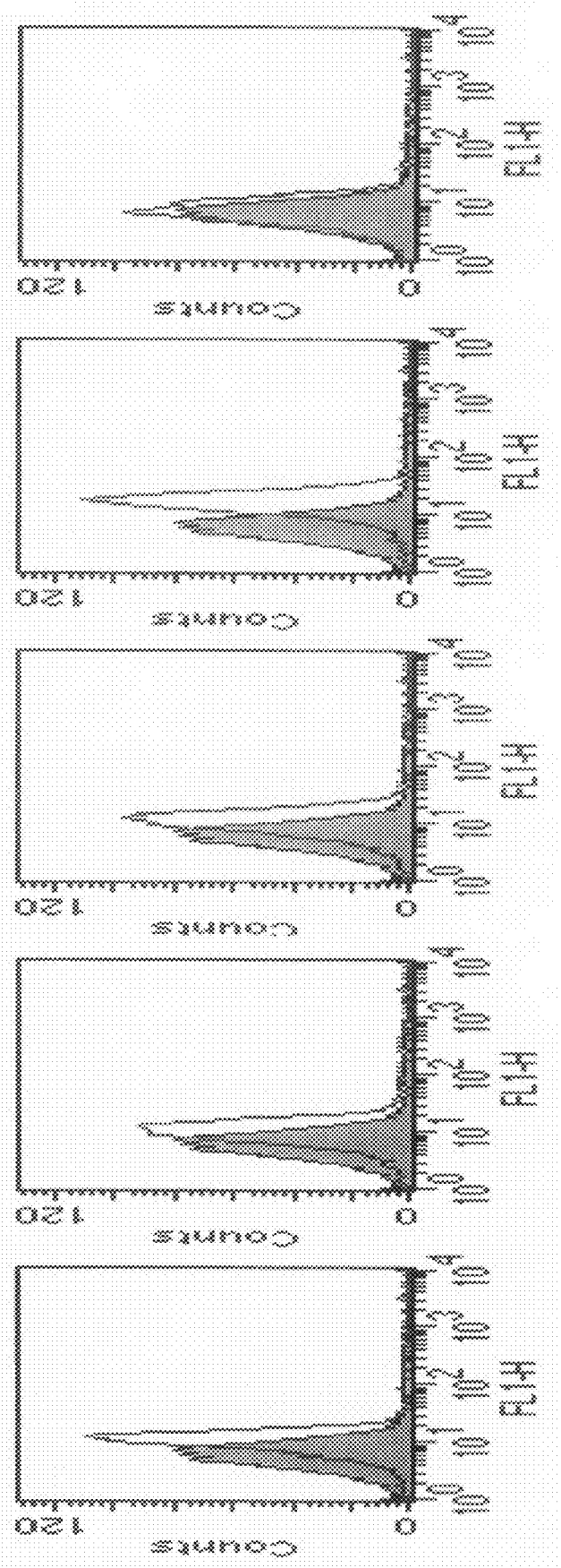
FIG. 3 shows the stained images of normal tissues by the anti-mouse α9 integrin antibodies.

For immunohistochemistry, various biological tissues were excised from mice and embedded in O.C.T. compound (Tissue Tech). After freezing in liquid nitrogen, the tissues were sliced on Cold Tome (Sakura) in 5 μm thick. After drying overnight in a stream of air, the tissue slices were fixed in acetone at −20° C. and non-specific binding was blocked with normal goat serum. Next, using the anti-α9 integrin antibody clone 12C4'58 as a primary antibody, the reaction was carried out in a 2 μg/ml concentration at room temperature for an hour, and a 500-fold dilution of biotinylated goat anti-Syrian hamster IgG antibody (Jackson) in PBS was added thereto as a secondary antibody, followed by reacting at room temperature for 30 minutes. After the reaction was carried out at room temperature for 30 minutes using Vector Stain ABC kit (Vector Laboratories), DAB+ Substrate Kit (Dako) was used in the reaction at room temperature for approximately 1 to 5 minutes for detection. The tissues were then nuclear stained with hematoxylin (Wako) and mounted using a cover glass and a mounting medium. Stained images of mouse brain, liver, lung and muscle are shown in FIG. 3. As shown by the summary list of stained images (FIG. 4), expression of the α9 integrin was observed in the cells from the brain choroid plexus, the vascular endothelium, smooth muscle and alveolar macrophage of the lung, hepatic sinusoidal cells, the vascular endothelium, smooth muscle and glomeruli of the kidney, the smooth muscle and lamina muscularis mucosa of the stomach, the vascular endothelium, myofibroblast and lymphatic vessel of the muscle, and the vascular endothelium, smooth muscle and arterial smooth muscle of the uterus, etc. These results reveal that the anti-α9 integrin antibodies discovered by the present invention can be used for immunostaining and can be expected as diagnostic agents.

Example 5

[Analysis of Cell Adhesion Inhibitory Effect]

In order to examine whether the established four anti-mouse α9 integrin antibodies have the cell adhesion inhibitory activity, cell adhesion inhibition test was performed using GRGDS (SEQ ID NO: 16), tenascin-C, the SVVYGLR peptide (SEQ ID NO: 15) and mouse α9/NIH3T3 cells. The RGD sequence contained in the GRGDS peptide (SEQ ID NO: 16) is a cell adhesion domain commonly present in many ECMs. The AEIDGIEL peptide (SEQ ID NO: 17), which is a cell adhesion domain of tenascin-C, can adhere to the α9 integrin but cannot adhere to the α4 integrin. The SVVYGLR peptide (SEQ ID NO: 15) of human OPN can adhere to the α4,α9 integrins. The adhesion inhibitory abilities of the respective anti-α9 integrin antibodies were examined for the cell adhesion of these three solid-phase peptides to mouse α9/NIH3T3 cells.

The SVVYGLR sequence (SEQ ID NO: 15) and GRGDS sequence (SEQ ID NO: 16) in the adhesion domain of OPN cells and the AEIDGIEL sequence (SEQ ID NO: 17) of tenascin-C were immobilized on a solid phase (10 μg/ml, 50 μl/well), and the α9/NIH3T3 cells ($1.0\times10^5$/ml), which had been previously reacted with the antibody in DMEM/0.25% BSA medium, were added to ELISA plates blocked with a blocking solution (0.5% BSA/PBS). After incubation was carried out at 37° C. for an hour, non-adherent cells were rinsed with PBS and adherent cells were fixed and stained with 0.5% Crystal Violet/20% methanol. The stained cells were allowed to stand at room temperature for 30 minutes and 20% acetic acid solution was added thereto to effect dissolution. The adhesion activity was quantified by measuring OD at 590 nm wavelength.

As a result, the α9 integrin could not inhibit all of the anti-α9 integrin antibodies in the GRGDS peptide (SEQ ID NO: 16) solid phase as shown in FIG. 5, since adhesion of the α9 integrin was independent on RGD. Where the AEIDGIEL peptide (SEQ ID NO: 17), which is a tenascin-C functional domain, and the SVVYGLR peptide (SEQ ID NO: 15), which is an OPN functional domain, were immobilized on a solid phase, marked inhibition of the cell adhesion was observed with the three clones 11L2B, 12C4'58 and 55A2C, whereas 18R18D rarely showed the inhibitory ability.

Figure 6:
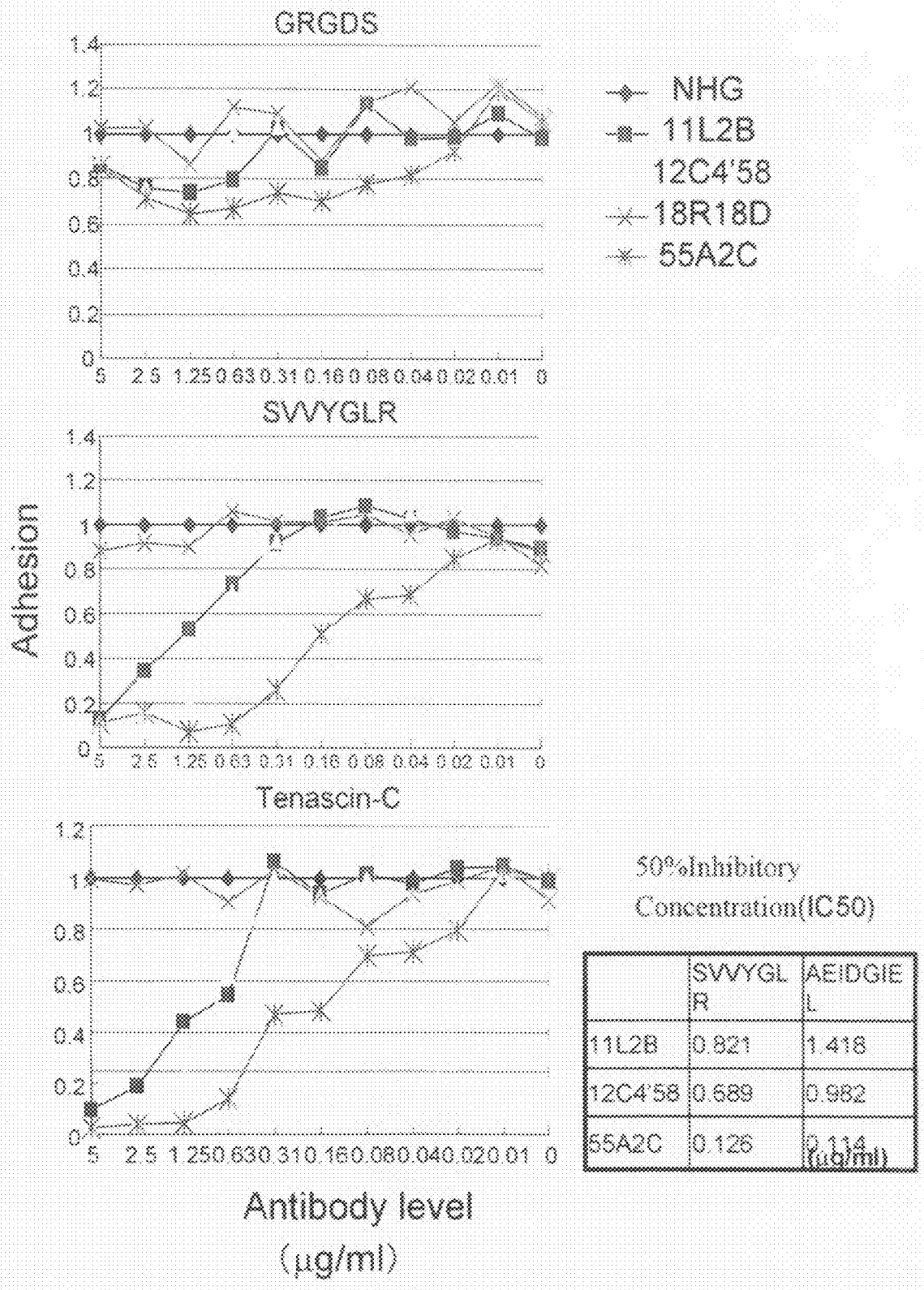
FIG. 6 shows a comparison in the cell adhesion inhibitory effects of the anti-mouse α9 integrin antibody clones. 'GRGDS' disclosed as SEQ ID NO: 16. 'SVVYGLR' disclosed as SEQ ID NO: 15. 'AEIDGIEL' disclosed as SEQ ID NO: 17.

Next, the three clones 11L2B, 12C4'58 and 55A2C which showed the inhibitory effects in FIG. 5 were compared in terms of the inhibitory effects. The solid phases of the AEIDGIEL peptide (SEQ ID NO: 17) and SVVYGLR peptide (SEQ ID NO: 15) were immobilized in 5 μg/ml, and the concentrations of the inhibitory antibodies were comparatively examined by the cell adhesion inhibition test. As shown in FIG. 6, 55A2C was found to show the highest inhibitory ability. The 50% inhibitory concentrations (IC50) are also shown in FIG. 6.

Example 6

[Epitope Analysis by Competitive Inhibition Test]

Figure 7:
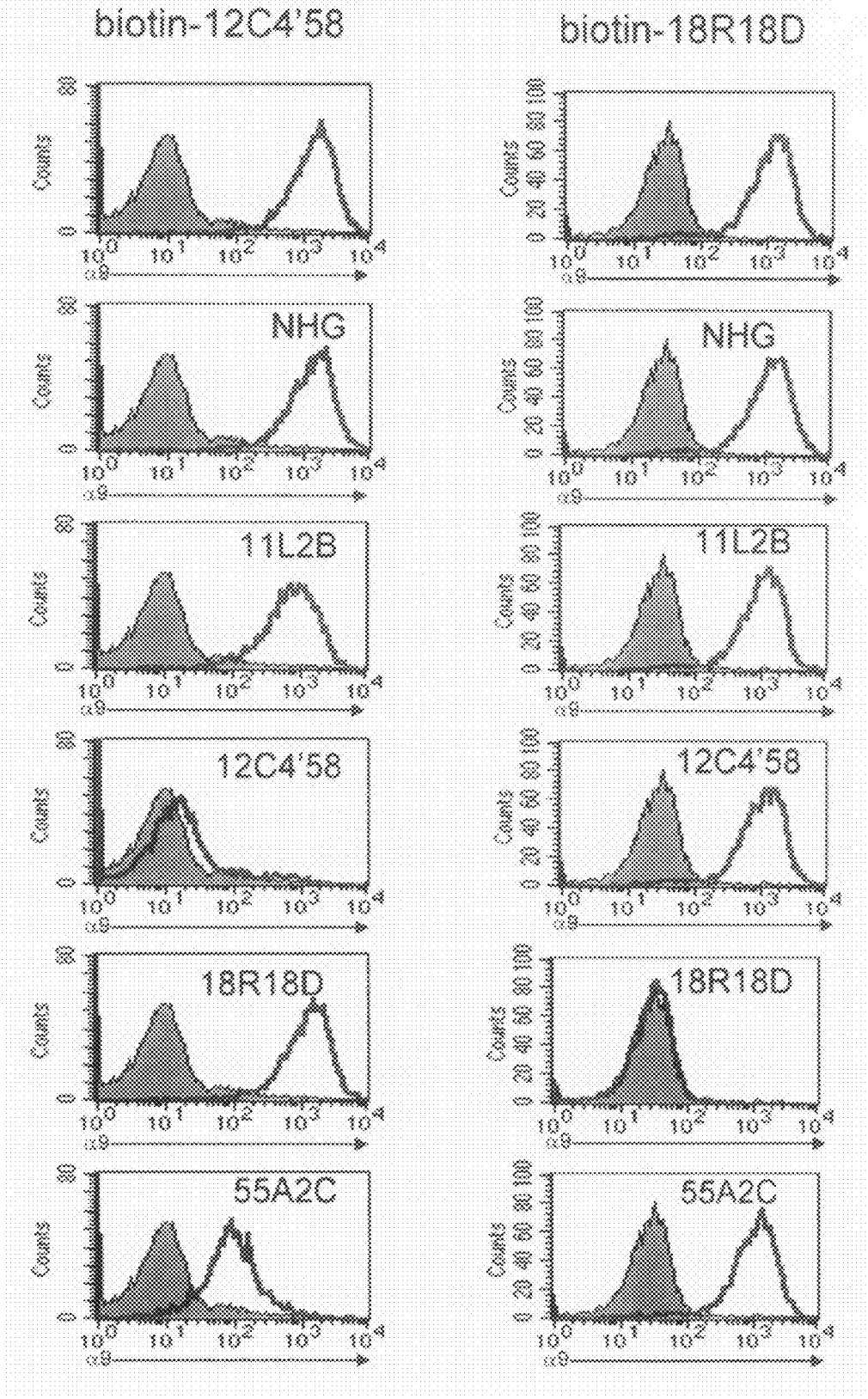
FIG. 7 shows the results of epitope analysis for the antibodies by a competitive inhibition test.

The results obtained by the cell adhesion inhibition test in EXAMPLE 5 indicate that there are differences in inhibitory activities of the respective anti-α9 integrin antibodies. This suggests that these antibodies recognize different epitopes on the α9 integrin, respectively. Thus, the antibodies were biotinylated and provided for epitope analysis by a competitive inhibition test. Using 12C4'58 and 18R18D as the biotinylated antibodies, differences in epitopes between these two clones and all other clones were examined. As shown in FIG. 7, in both antibodies, the competitive binding of the biotinylated antibodies was completely inhibited by competition with the same clone. When biotinylated 18R18D was used, the binding could not be inhibited in all clones. Turning to 12C4'58, it is noted from 55A2C that the binding was partially inhibited, suggesting that epitopes would partially overlap between 12C4'58 and 55A2C.

Example 7

[Expression Analysis of α9 Integrin in Culture Cell Line]

Figure 8:
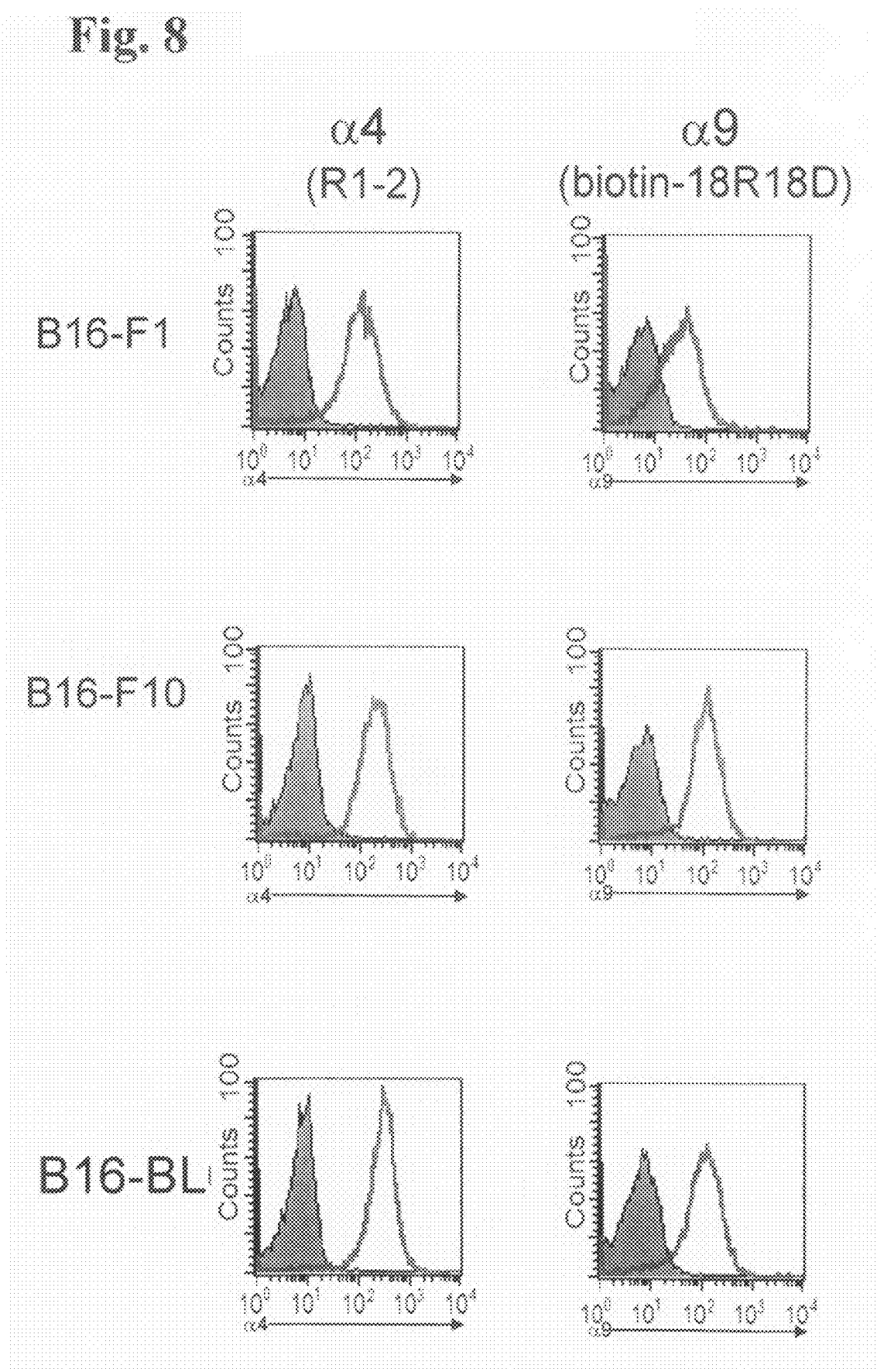
FIG. 8 shows the results of expression analysis of the α4 and α9 integrins in the mouse melanoma cell line.

In order to examine the expression of α9 integrin on culture cells, FACS. analysis was performed on mouse melanoma culture cells B16-F1, B16-F10 and B16-BL6. As a result, expression of the α9 integrin could be confirmed in all of the B16-F1, B16-F10 and B16-BL6 cells, as shown in FIG. 8.

Since the expression was also confirmed at a low level of human periphery blood mononuclear cells, FACS analysis was performed on myelomonocytic leukemia cells WEHI-3B and macrophage-like cells RAW264.7. As shown in FIG. 9, the expression could not be detected on the WEHI-3B cells, whereas strong expression could be confirmed on the RAW264.7 cells.

Example 8

[Expression Analysis of α9 Integrin in Neutrophils]

Figure 10:
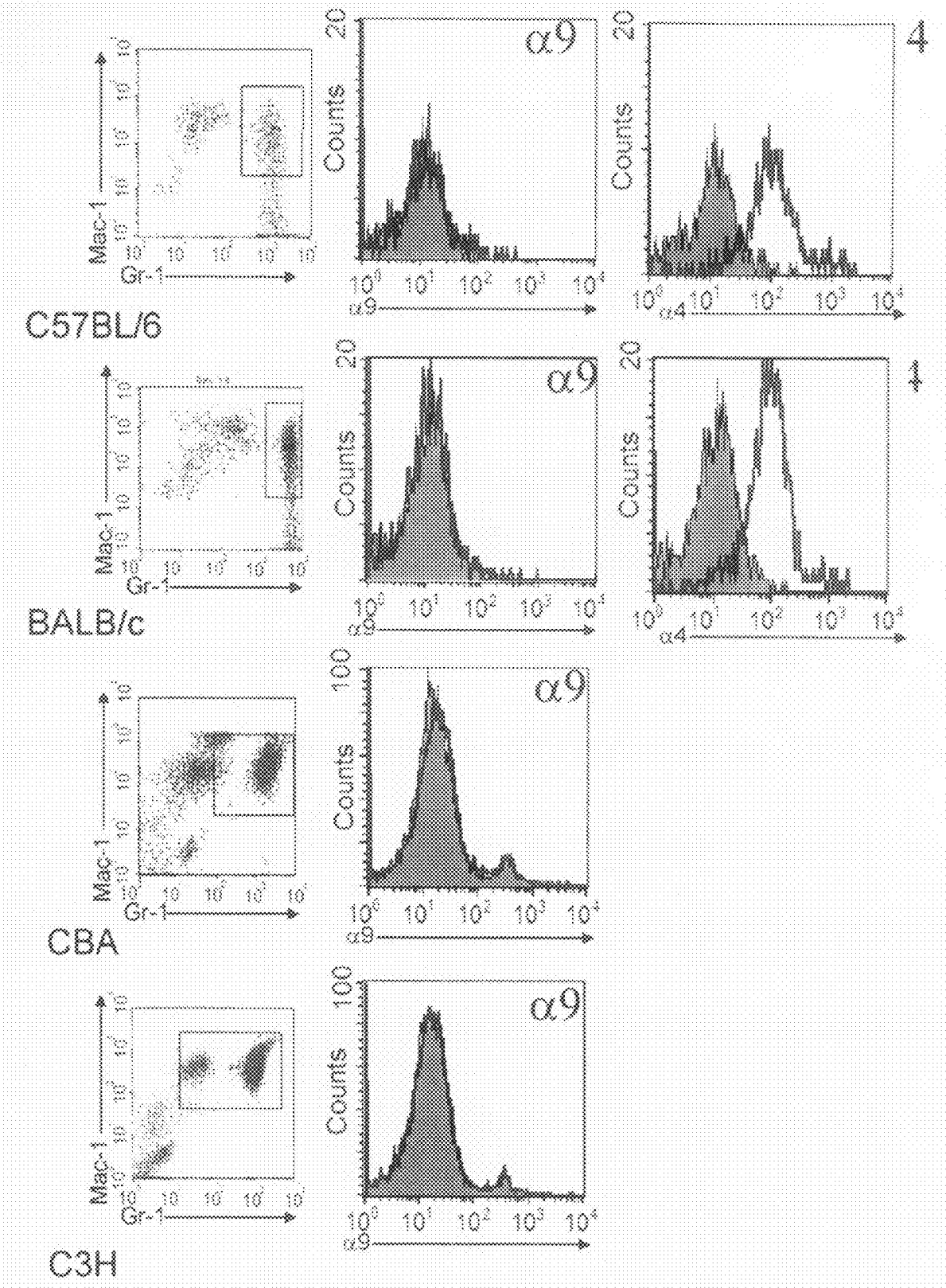
FIG. 10 shows the results of FACS analysis of mouse neutrophils.

It is already reported that the α9 integrin is overexpressed in human neutrophils. To analyze the α9 integrin expression in mouse neutrophils, thioglycolate elicited peritoneal cells were recovered and used to analyze the expression in mouse neutrophils. The Mac-$1^+$Gr-$1^+$ cells were used as neutrophils and the α9 integrin expression in this cell population was analyzed by FACS. As shown in FIG. 10, any integrin expression could not be confirmed in all strains of mice: C57BL/6, BALB/c, CBA and C3H. The results revealed that normally the α9 integrin was not expressed in mouse neutrophils.

Example 9

[Expression Pattern Analysis of α4 Integrin and α9 Integrin]

The α4 integrin and α9 integrin belong to the same integrin subfamily and share many ligands, suggesting that these integrins would fulfill similar functions. It is also reported by analysis on an mRNA level that NKT cells present in intrahepatic leukocytes from mice co-expressed both α4 and α9 integrins (Diao, H., Kon, S., Iwabuchi, K., Kimura, C., Morimoto, J., Ito, D., Segawa, T., Maeda, M., Hamuro, J., Nakayama, T., Taniguchi, M., Yagita, H., Van Kaer, L., Onoe, K., Denhardt, D., Rittling, S., T. U. 2004. Osteopontin as a mediator of NKT cell function in T cell-mediated liver diseases. Immunity, 21: 539-50)). In order to confirm whether both α4 and α9 integrins were expressed actually on the same cell, liver infiltrating leukocytes from mice were separated and subjected to double staining with both integrin antibodies. As a result, the α4 integrin was expressed by about 39% of the whole intrahepatic leukocytes and the α9 integrin was expressed by about 12% of the total infiltrating leukocytes, as shown in FIG. 11. The α9 integrin was found to be expressed by about 74% of the α4 integrin-expressed cells.

Example 10

[Adhesion Pattern Analysis of OPN to B16-BL6 Cells]

Many cells including the B16-BL6 cells co-express the α4 integrin and the α9 integrin. In addition, the α4 integrin and the α9 integrin share ligands such as OPN, VCAM-1, etc. It is therefore expected that by a mere inhibition of the α4 integrin functions, which is now becoming clinically arresting, the functions will be compensated for by the α9 integrin. Thus, synergistic effects with the effect of inhibiting adhesion of the SVVYGLR peptide (SEQ ID NO: 15) to the B16-BL6 cells by concomitant use of the anti-α4 integrin antibody and the anti-α9 integrin antibody were examined.

Specifically, adhesion inhibitory effects on the B 16-BL6 cells by the anti-α4, α9 integrin antibodies were examined by a cell adhesion test on a solid phase (5 μg/ml) of the SVVYGLR sequence (SEQ ID NO: 15). Upon adhesion, 1 mM MnCl$_2$ was added to the medium for reaction. The reaction was carried out using as antibodies the anti-α4 integrin antibody (clone R1-2) (Pharmingen) and the anti-α9 integrin antibody (clone 11L2B). Normal rat antibody (NRG) was used as a control antibody for the anti-α4 integrin antibody and normal hamster antibody (NHG) as a control antibody for the anti-α9 integrin antibody. The inhibitory activity was assayed using 50 μg/ml of the antibody and 25 μg each/ml in concomitant use of two antibodies.

As a result, the inhibitory effect could hardly be detected when the anti-α4 integrin antibody or the anti-α9 integrin antibody was used alone, as shown in FIG. 12. In contrast, when the anti-α4 integrin antibody was used in combination with the anti-α9 integrin antibody, the inhibitory effect was observed. The results suggest that the α4 integrin antibody and the α9 integrin antibody have almost complete cell adhesion ability to the SVVYGLR sequence (SEQ ID NO: 15) even in their single use. It is shown that both α4 integrin- and α9 integrin-expressed cells (neutrophils, NKT cells, etc.) are associated with the onset of diseases. Moreover, the both integrins share many ligands. Taking these into account, therapeutic effects can be achieved more efficiently by concomitant use of the anti-α9 integrin antibody and the anti-α4 integrin antibody, suggesting that such use will provide a new therapeutic approach.

Example 11

[Therapeutic Effects on Hepatitis by Anti-α9 Integrin Antibodies]

Figure 13:
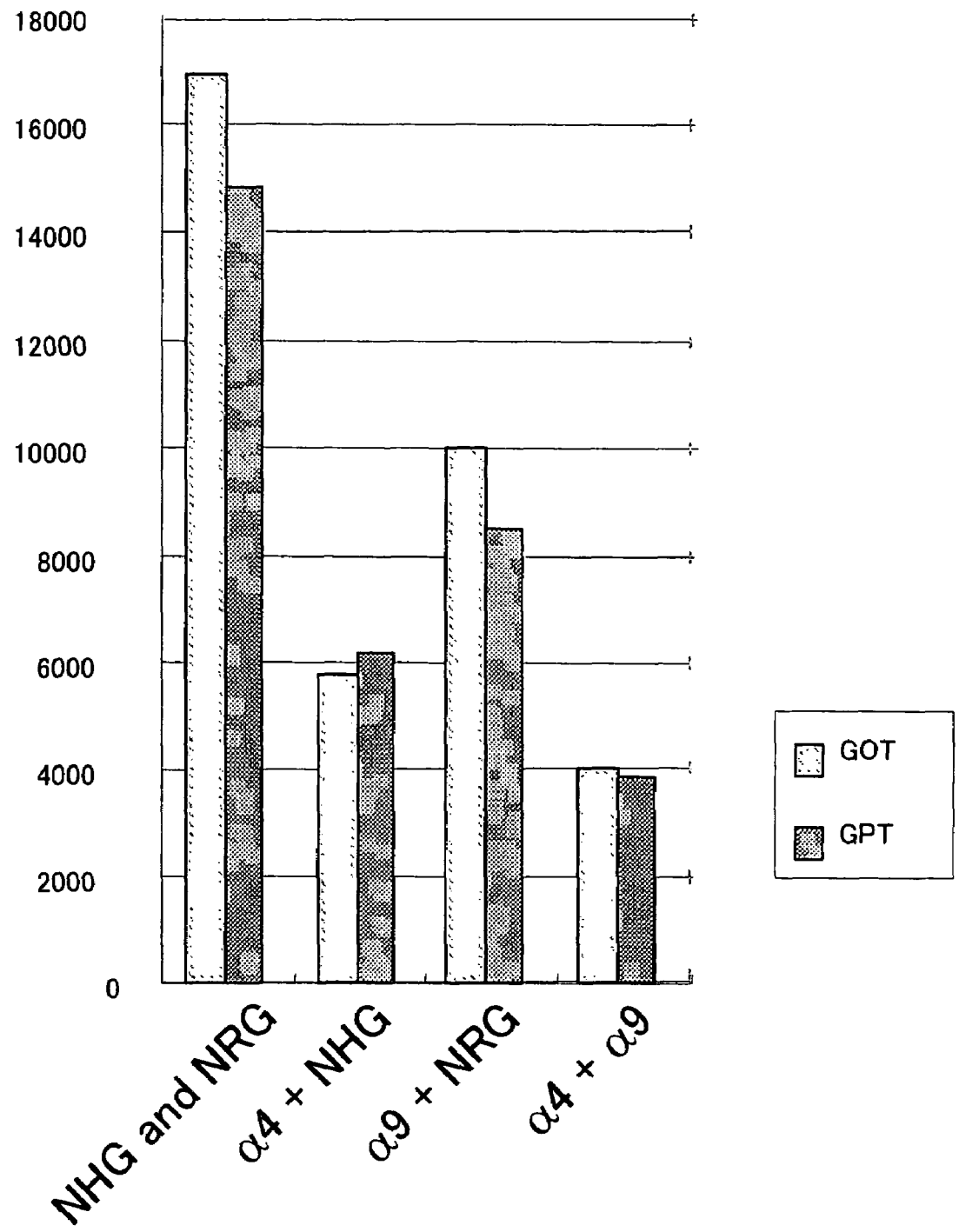
FIG. 13 shows therapeutic effects on hepatitis by the anti-α4 integrin antibodies and the anti-α9-integrin antibodies.

The inventors have demonstrated so far that hepatitis can be treated by inhibiting the OPN functions (Patent Literature 1). Consequently, clinical trials were conducted using the anti-α9 integrin antibody clone 11L2B and the anti-α4 integrin antibody clone R1-2 (Pharmingen). In hepatitis, the blood AST and ALT levels were measured using GPT/ALT-PIII and GOT/AST-PIII (Fuji Film), 12 hours after 200 μg of concanavalin A (Con A) (Vector) was intravenously injected. Three hours before the Con A injection, 200 μg of the antibody was administered. As shown in FIG. 13, the AST and ALT levels were found to be decreased by the anti-α9 integrin antibody, and the therapeutic effects could be noted. In addition, the therapeutic effects could be boosted by concomitant use with the anti-α4 integrin antibody. The results reveal that hepatitis could be treated by the anti-α9 integrin antibody.

Example 12

[Change in MMP-13 by Anti-α9 Integrin Antibody Using Tendon Fibroblasts]

Tendon fibroblasts were recovered from mouse patellar tendons and the expression of α9 integrin was examined by FACS and cell staining. Clone 18R18D was used as the anti-α9 integrin antibody and R1-2 was used as the anti-α4 integrin antibody. As shown in FIG. 14, the α9 integrin was found to be expressed in tendon fibroblasts. The α4 integrin was not expressed.

Figure 15:
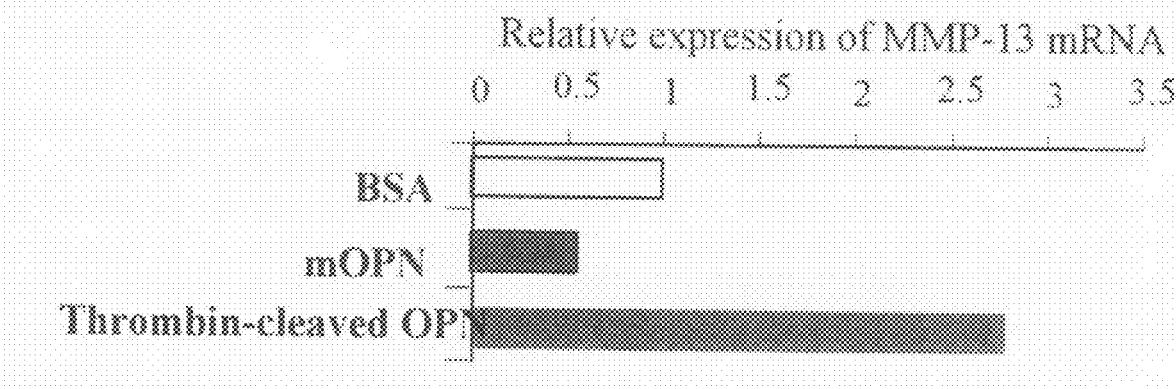
FIG. 15 shows that the MMP-13 mRNA transcription in tendon fibroblasts increases by thrombin-cleaved OPN.
Figure 16:
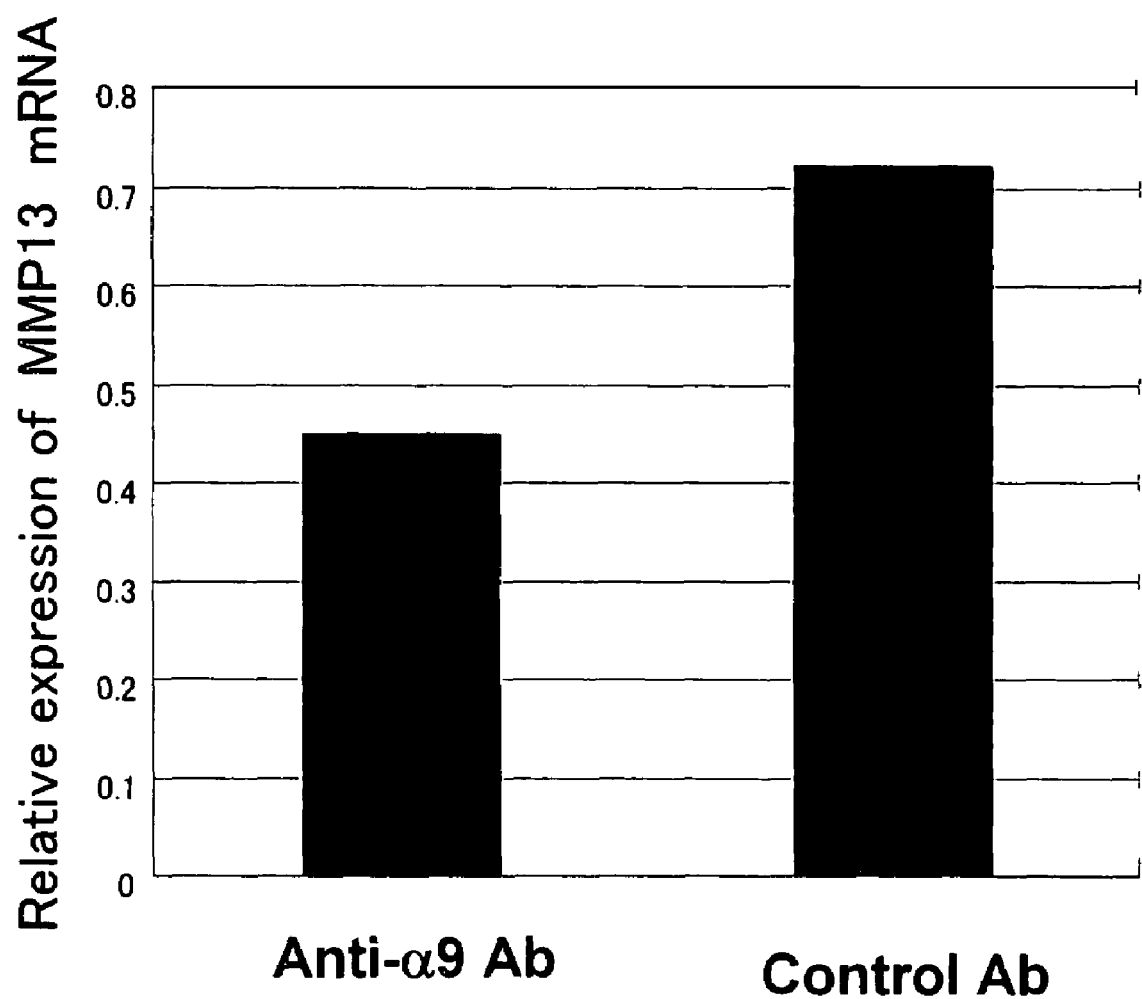
FIG. 16 shows that the MMP-13 mRNA transcription from tendon fibroblasts is inhibited by the anti-α9 integrin antibody.

Recombinant full-length OPN and thrombin-cleaved OPN (each in 10 μg/ml) were immobilized on a solid phase and tendon fibroblasts were incubated for 48 hours to quantify the MMP-13 mRNA level using real-time PCR. It was observed that stimulation of tendon fibroblasts with thrombin-cleaved OPN increased transcription of MMP-13 (FIG. 15). Next, the anti-α9 integrin antibody 55A2C was added to the culture in 30 μg/ml to monitor changes of MMP-13 mRNA level. As shown in FIG. 16, it was found that the MMP-13 transcription level was inhibited by the anti-α9 integrin antibody (clone 55A2C). Hamster IgG was used as a control antibody.

MMP-13 is also termed collagenase. In mouse collagenase, MMP-13 is a typical MMP, whereas MMP-1, MMP-8 and MMP-13 are involved in human. It is demonstrated that MMP-13 is strongly associated with an exacerbation of arthritis (especially rheumatoid arthritis (RA) or osteoarthritis (OA)) (Skotnicki, J. S., DiGrandi, M. J., Levin, J. I., Design strategies for the identification of MMP-13 and TACE inhibitors. Curr. Opin. Drug Discov. Devel. (2003) 6: 742-59, Review). This finding that transcription of MMP-13 can be inhibited by the anti-α9 integrin antibody strongly suggests that arthritis can be treated by using the anti-α9 integrin antibodies.

Example 13

[Functions of Anti-α9 Integrin Antibodies in Growth of Cancer Cell Line]

Figure 17:
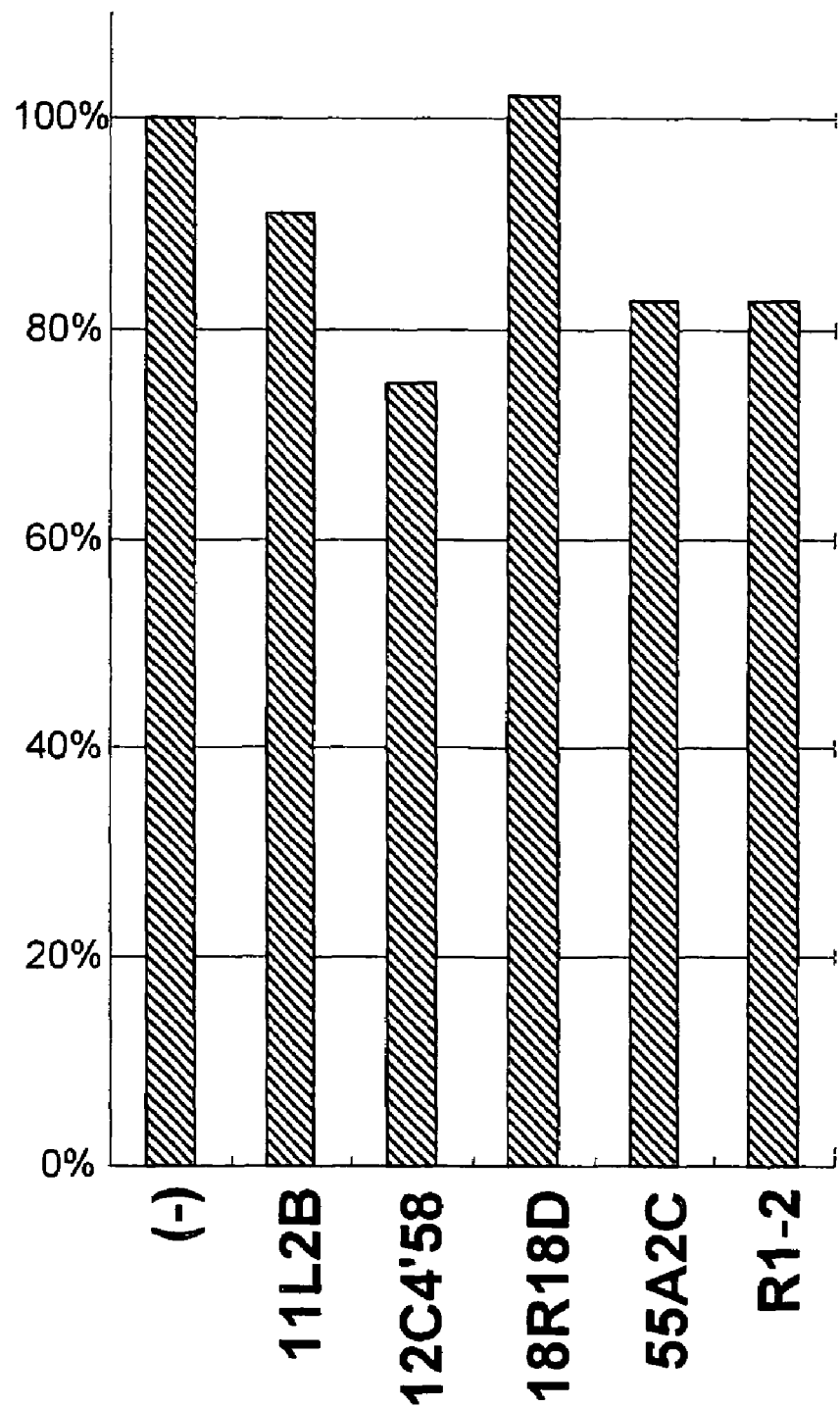
FIG. 17 shows that growth of the B16-BL6 cells was inhibited by the anti-α9 integrin antibodies.

As shown in FIG. 2, the α9 integrin is abundantly expressed in B16-BL6. It is also reported that MMP-13 is associated with an exacerbation of cancer (Ala-aho, R., Kahari, V. M., Collagenases in cancer. Biochimie (2005) 87: 273-86, Review). Accordingly, cell growth inhibitory activities of the established four anti-mouse α9 integrin antibodies against cancer cells were assayed. The B16-BL6 cells were prepared on a 96-well plate for cell culture (Becton Dickinson) at $5 \times 10^4$ cells/mL in 10% FCS/DMEM. After 10 μg/ml of the anti-mouse α9 integrin antibody and anti-mouse α4 integrin antibody were added, 100 μL each of the cell-antibody suspension was added to each well. Incubation was conducted at 37° C. for 24 hours under 5% $CO_2$, and 10 μL each of Cell Counting Kit 8 (Dojin Kagaku Kenkyu-sho) was added, followed by incubation at 37° C. for an hour under 5% $CO_2$. Absorbance at O.D. 450 was measured and the cell count was quantitatively analyzed. As shown in FIG. 17, 12C4'58 gave the highest inhibitory activity and inhibited the growth of B16-BL6 cells by about 35%. Both 55A2C and R1-2 could inhibit the growth by about 20%.

Figure 18:
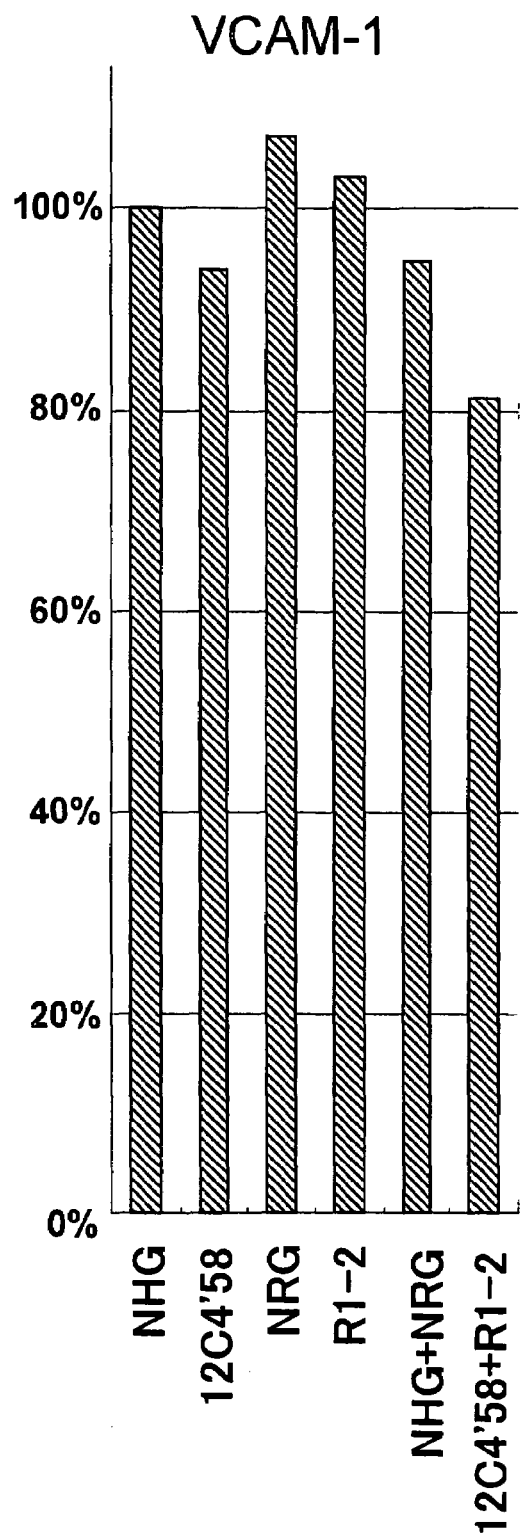
FIG. 18 shows that growth of the B16-BL6 cells induced by VCAM-1 stimulation was inhibited by concomitant use of the anti-α9 and anti-α4 integrin antibodies.

Next, for analysis of inhibitory effects against cell growth under conditions closer to the in vivo conditions, VCAM-1 was immobilized on a solid phase and assayed in a similar fashion. VCAM-1 is a ligand for α9 integrin and a recombinant soluble form of VCAM-1 protein, rhVCAM-1-Fc chimera (Roche), was used. Using the rhVCAM-1-Fc chimera immobilized on a solid phase with 10 μg/mL, non-specific reaction was blocked with 0.5% BSA/PBS. The chimera was added in a concentration of 10 μg/ml in single use of the antibody, and in 5 μg each/ml in concomitant use. Thereafter, the same procedures as in FIG. 17 were followed. As a result, the effect was not obtained at all or only an imperceptible effect was obtained by single administration of 12C4'58 and by single use of the α4 inhibitory antibody clone R1-2, whereas in simultaneous administration of 12C4'58 with R1-2 the cell growth inhibitory effect showed a marked increase by about 20%, as shown in FIG. 18.

Example 14

[Analysis of the Functions of Anti-human α9 Integrin Antibodies]

Whether the anti-human α9 integrin antibodies were usable for FACS was examined using human α9/CHO-K1 cells, CHO-K1 cells and human neutrophils endogenously expressing the α9 integrin. In human neutrophils, FACS analysis was conducted in a similar manner to FIG. 2, except that non-specific reaction with the Fc receptor was blocked with 50% goat serum. FITC-labeled anti-mouse IgG antibody was used as a secondary antibody. As a result, all of the anti-human α9 integrin antibodies could detect the α9 integrin on human α9/CHO-K1 and human neutrophils. None of the antibodies reacted with human α4/CHO-K1 cells. These results reveal that all of the anti-human α9 integrin antibodies could detect the human α9 integrin proteins expressed on cells using FACS.

Example 15

Using OPN and tenascin-C functional peptide as ligands for the α9 integrin, a cell adhesion test was carried out. Human α9/CHO-K1 cells were used to examine the inhibitory ability of various anti-α9 integrin antibodies. The peptide was immobilized on a solid phase with 5 μg/ml and inhibition was examined with 5 μg/ml of the antibody. As shown in FIG. 20, the clone 21C5 exhibited the most effective inhibitory activity in the adhesion inhibition test against OPN, whereas the inhibitory effects of 1K11 and 24I11 were low. Turning to the adhesion inhibitory ability against tenascin-C, Y9A2 showed the most effective inhibitory activity. The four anti-α9 integrin antibody clones produced herein had little inhibitory activity against tenascin-C.

The neutralizing antibody Y9A2 against human α9 integrin was already reported and is commercially available from Chemicon. Y9A2 is produced from the human α9 integrin gene-transfected mouse fibroblast cell line, L cells, by a conventional immunization method (intraperitoneal injection). The anti-human α9 integrin antibodies of the present invention are produced by the subtractive immunization technique, which is a different immunization method. Further as shown in FIG. 19, the clone 21C5 is different in FACS pattern from human α9/CHO-K1 cells, and is further different in profiles of the inhibitory effects in the cell adhesion test as shown in FIG. 20. It is thus considered that the four anti-α9 integrin antibody clones produced herein are different in epitopes from Y9A2.

SUMMARY

For purposes of producing the antibodies inhibiting the mouse α9 integrin functions and for elucidation of the α9 integrin functions in diseases/pathological conditions, the four monoclonal antibodies against the mouse α9 integrin and the four anti-human α9 integrin antibodies were prepared. Studies using these antibodies were able to reveal the following.

(1) The four anti-mouse α9 integrin antibodies produced were all available for FACS analysis and had distinctly different cell adhesion inhibitory abilities.

(2) The anti-mouse α9 integrin antibody clone 12C4'58 was found to be available for immunostaining.

(3) The α9 integrin was expressed in macrophage-like RAW264.7 cells or melanoma cells B16-F1, B16-F10 and B16-BL6. Expression of the α9 integrin on mouse neutrophils was not observed but could be confirmed in human, indicating that there are differences between species in expression of the α9 integrin on neutrophils. Some of the cell groups expressing the α9 integrin were found from the B220$^-$CD3$^-$ cell group and B220$^+$CD3$^+$ cell group of spleen cells. The α9 integrin expression of liver infiltrating leukocytes was abundantly observed on the α4 integrin expression cells.

(4) Where the α9 and α4 integrins are co-present and a ligand is recognized by both of them, the adhesion ability was complementary to one another.

(5) Therapeutic effects on hepatitis by the anti-mouse α9 integrin antibodies could be found and the effect was enhanced by the anti-mouse α4 integrin antibodies.

(6) It was found that the α9 integrin was expressed on tendon fibroblasts and that stimulation of tendon fibroblasts by thrombin-cleaved OPN enhanced MMP-13 expression. The enhanced MMP-13 was found to be inhibited by the anti-α9 integrin antibodies.

(7) It was found that the growth of B16-BL6 cells could be inhibited by the anti-α9 integrin antibodies. In addition, the cell growth by VCAM-1 stimulation showed a more enhanced growth inhibitory effect by co-administration of the anti-α9 integrin antibody simultaneously with the anti-α4 integrin antibody, as compared to single administration of the antibody.

(8) The four anti-human α9 integrin antibodies produced are all available for FACS analysis and had distinctly different cell adhesion inhibitory abilities. Since the FACS and adhesion inhibition test showed different reactivities from the existing anti-human α9 integrin antibody Y9A2, it was considered that their epitopes would be different.

INDUSTRIAL APPLICABILITY

The monoclonal antibodies of the present invention inhibit the function of α9 integrin to exhibit therapeutic effects on cancer, e.g., the growth or metastasis of cancer cells, and an inflammatory disease, e.g., rheumatoid arthritis, osteoarthritis, hepatitis, bronchial asthma, fibrosis, diabetes mellitus, cancer metastasis, arteriosclerosis, multiple sclerosis, granuloma, an inflammatory bowel disease (ulcerative colitis and Crohn's disease), an autoimmune disease, and the like. The pharmaceutical composition comprising both the anti-α9 integrin antibody and anti-α4 integrin antibody of the present invention exerts more improved therapeutic effects on cancer and an inflammatory disease. The monoclonal antibodies of the present invention also recognize the mouse α9 integrin and can be used for animal tests using mice.

---

The invention claimed is:

1. A monoclonal antibody, which is produced by a hybridoma designated by Accession No. FERM BP-10195, FERM BP-10196, FERM BP-10197 or FERM BP-10198.

2. A hybridoma, which is designated by Accession No. FERM BP-10195, FERM BP-10196, FERM BP-10197 or FERM BP-10198.

3. A pharmaceutical composition for treating hepatitis, comprising the monoclonal antibody according to claim 1.

4. A pharmaceutical composition according to claim 3, further comprising an anti-α4 integrin antibody.

5. A method for treating hepatitis comprising administering the monoclonal antibody according to claim 1 to a patient in need thereof.

6. The method according to claim 5, wherein an anti-α4 integrin antibody is administered concomitantly with said monoclonal antibody.

* * * * *

SEQUENCE LISTING

<160> NUMBER OF SEQ ID NOS: 17

<210> SEQ ID NO 1
<211> LENGTH: 1035
<212> TYPE: PRT
<213> ORGANISM: Homo sapiens

<400> SEQUENCE: 1

```
Met Gly Gly Pro Ala Ala Pro Arg Gly Ala Gly Arg Leu Arg Ala Leu
1               5                   10                  15

Leu Leu Ala Leu Val Val Ala Gly Ile Pro Ala Gly Ala Tyr Asn Leu
                20                  25                  30

Asp Pro Gln Arg Pro Val His Phe Gln Gly Pro Ala Asp Ser Phe Phe
            35                  40                  45

Gly Tyr Ala Val Leu Glu His Phe His Asp Asn Thr Arg Trp Val Leu
    50                  55                  60

Val Gly Ala Pro Lys Ala Asp Ser Lys Tyr Ser Pro Ser Val Lys Ser
65                  70                  75                  80

Pro Gly Ala Val Phe Lys Cys Arg Val His Thr Asn Pro Asp Arg Arg
                85                  90                  95

Cys Thr Glu Leu Asp Met Ala Arg Gly Lys Asn Arg Gly Thr Ser Cys
            100                 105                 110

Gly Lys Thr Cys Arg Glu Asp Arg Asp Asp Glu Trp Met Gly Val Ser
        115                 120                 125

Leu Ala Arg Gln Pro Lys Ala Asp Gly Arg Val Leu Ala Cys Ala His
    130                 135                 140

Arg Trp Lys Asn Ile Tyr Tyr Glu Ala Asp His Ile Leu Pro His Gly
145                 150                 155                 160

Phe Cys Tyr Ile Ile Pro Ser Asn Leu Gln Ala Lys Gly Arg Thr Leu
                165                 170                 175

Ile Pro Cys Tyr Glu Glu Tyr Lys Lys Lys Tyr Gly Glu Glu His Gly
            180                 185                 190

Ser Cys Gln Ala Gly Ile Ala Gly Phe Phe Thr Glu Glu Leu Val Val
        195                 200                 205

Met Gly Ala Pro Gly Ser Phe Tyr Trp Ala Gly Thr Ile Lys Val Leu
    210                 215                 220

Asn Leu Thr Asp Asn Thr Tyr Leu Lys Leu Asn Asp Glu Val Ile Met
225                 230                 235                 240

Asn Arg Arg Tyr Thr Tyr Leu Gly Tyr Ala Val Thr Ala Gly His Phe
                245                 250                 255

Ser His Pro Ser Thr Ile Asp Val Val Gly Gly Ala Pro Gln Asp Lys
            260                 265                 270

Gly Ile Gly Lys Val Tyr Ile Phe Arg Ala Asp Arg Arg Ser Gly Thr
        275                 280                 285

Leu Ile Lys Ile Phe Gln Ala Ser Gly Lys Lys Met Gly Ser Tyr Phe
    290                 295                 300

Gly Ser Ser Leu Cys Ala Val Asp Leu Asn Gly Asp Gly Leu Ser Asp
305                 310                 315                 320

Leu Leu Val Gly Ala Pro Met Phe Ser Glu Ile Arg Asp Glu Gly Gln
                325                 330                 335
```

-continued

```
Val Thr Val Tyr Ile Asn Arg Gly Asn Gly Ala Leu Glu Glu Gln Leu
            340                 345                 350

Ala Leu Thr Gly Asp Gly Ala Tyr Asn Ala His Phe Gly Glu Ser Ile
            355                 360                 365

Ala Ser Leu Asp Asp Leu Asp Asn Asp Gly Phe Pro Asp Val Ala Ile
370                 375                 380

Gly Ala Pro Lys Glu Asp Asp Phe Ala Gly Ala Val Tyr Ile Tyr His
385                 390                 395                 400

Gly Asp Ala Gly Gly Ile Val Pro Gln Tyr Ser Met Lys Leu Ser Gly
            405                 410                 415

Gln Lys Ile Asn Pro Val Leu Arg Met Phe Gly Gln Ser Ile Ser Gly
            420                 425                 430

Gly Ile Asp Met Asp Gly Asn Gly Tyr Pro Asp Val Thr Val Gly Ala
            435                 440                 445

Phe Met Ser Asp Ser Val Val Leu Leu Arg Ala Arg Pro Val Ile Thr
            450                 455                 460

Val Asp Val Ser Ile Phe Leu Pro Gly Ser Ile Asn Ile Thr Ala Pro
465                 470                 475                 480

Gln Cys His Asp Gly Gln Gln Pro Val Asn Cys Leu Asn Val Thr Thr
            485                 490                 495

Cys Phe Ser Phe His Gly Lys His Val Pro Gly Glu Ile Gly Leu Asn
            500                 505                 510

Tyr Val Leu Met Ala Asp Val Ala Lys Lys Glu Lys Gly Gln Met Pro
            515                 520                 525

Arg Val Tyr Phe Val Leu Leu Gly Glu Thr Met Gly Gln Val Thr Glu
            530                 535                 540

Lys Leu Gln Leu Thr Tyr Met Glu Glu Thr Cys Arg His Tyr Val Ala
545                 550                 555                 560

His Val Lys Arg Arg Val Gln Asp Val Ile Ser Pro Ile Val Phe Glu
            565                 570                 575

Ala Ala Tyr Ser Leu Ser Glu His Val Thr Gly Glu Glu Arg Glu
            580                 585                 590

Leu Pro Pro Leu Thr Pro Val Leu Arg Trp Lys Lys Gly Gln Lys Ile
            595                 600                 605

Ala Gln Lys Asn Gln Thr Val Phe Glu Arg Asn Cys Arg Ser Glu Asp
            610                 615                 620

Cys Ala Ala Asp Leu Gln Leu Gln Gly Lys Leu Leu Leu Ser Ser Met
625                 630                 635                 640

Asp Glu Lys Thr Leu Tyr Leu Ala Leu Gly Ala Val Lys Asn Ile Ser
            645                 650                 655

Leu Asn Ile Ser Ile Ser Asn Leu Gly Asp Asp Ala Tyr Asp Ala Asn
            660                 665                 670

Val Ser Phe Asn Val Ser Arg Glu Leu Phe Phe Ile Asn Met Trp Gln
            675                 680                 685

Lys Glu Glu Met Gly Ile Ser Cys Glu Leu Leu Glu Ser Asp Phe Leu
            690                 695                 700

Lys Cys Ser Val Gly Phe Pro Phe Met Arg Ser Lys Ser Lys Tyr Glu
705                 710                 715                 720

Phe Ser Val Ile Phe Asp Thr Ser His Leu Ser Gly Glu Glu Val
            725                 730                 735

Leu Ser Phe Ile Val Thr Ala Gln Ser Gly Asn Thr Glu Arg Ser Glu
            740                 745                 750

Ser Leu His Asp Asn Thr Leu Val Leu Met Val Pro Leu Met His Glu
```

-continued

```
                    755                 760                 765
Val Asp Thr Ser Ile Thr Gly Ile Met Ser Pro Thr Ser Phe Val Tyr
    770                 775                 780

Gly Glu Ser Val Asp Ala Ala Asn Phe Ile Gln Leu Asp Asp Leu Glu
785                 790                 795                 800

Cys His Phe Gln Pro Ile Asn Ile Thr Leu Gln Val Tyr Asn Thr Gly
                    805                 810                 815

Pro Ser Thr Leu Pro Gly Ser Ser Val Ser Ile Ser Phe Pro Asn Arg
                820                 825                 830

Leu Ser Ser Gly Gly Ala Glu Met Phe His Val Gln Glu Met Val Val
            835                 840                 845

Gly Gln Glu Lys Gly Asn Cys Ser Phe Gln Lys Asn Pro Thr Pro Cys
850                 855                 860

Ile Ile Pro Gln Glu Gln Asn Ile Phe His Thr Ile Phe Ala Phe
865                 870                 875                 880

Phe Thr Lys Ser Gly Arg Lys Val Leu Asp Cys Glu Lys Pro Gly Ile
                885                 890                 895

Ser Cys Leu Thr Ala His Cys Asn Phe Ser Ala Leu Ala Lys Glu Glu
            900                 905                 910

Ser Arg Thr Ile Asp Ile Tyr Met Leu Leu Asn Thr Glu Ile Leu Lys
        915                 920                 925

Lys Asp Ser Ser Val Ile Gln Phe Met Ser Arg Ala Lys Val Lys
930                 935                 940

Val Asp Pro Ala Leu Arg Val Val Glu Ile Ala His Gly Asn Pro Glu
945                 950                 955                 960

Glu Val Thr Val Val Phe Glu Ala Leu His Asn Leu Glu Pro Arg Gly
                965                 970                 975

Tyr Val Gly Trp Ile Ile Ala Ile Ser Leu Leu Val Gly Ile Leu
            980                 985                 990

Ile Phe Leu Leu Leu Ala Val Leu  Leu Trp Lys Met Gly  Phe Phe Arg
        995                 1000                1005

Arg Arg  Tyr Lys Glu Ile Ile  Glu Ala Glu Lys Asn  Arg Lys Glu
    1010                1015                1020

Asn Glu  Asp Ser Trp Asp Trp  Val Gln Lys Asn Gln
    1025                1030                1035

<210> SEQ ID NO 2
<211> LENGTH: 1036
<212> TYPE: PRT
<213> ORGANISM: Mus musculus

<400> SEQUENCE: 2

Met Gly Gly Pro Ala Ala Ala Arg Thr Gly Ala Gly Leu Arg Ala
1               5                   10                  15

Leu Leu Leu Ala Leu Val Ala Ala Gly Val Pro Ala Gly Ala Tyr Asn
                20                  25                  30

Leu Asp Ala Gln Arg Pro Val Arg Phe Gln Gly Pro Ser Gly Ser Phe
            35                  40                  45

Phe Gly Tyr Ala Val Leu Glu His Phe His Asp Asn Thr Arg Trp Val
    50                  55                  60

Leu Val Gly Ala Pro Lys Ala Asp Ser Lys Tyr Ser Thr Ser Val Lys
65                  70                  75                  80

Ser Pro Gly Ala Val Phe Lys Cys Arg Val His Thr Asn Pro Asp Arg
                85                  90                  95
```

```
Arg Cys Thr Glu Leu Asp Met Ala Arg Gly Arg Thr Arg Gly Ala Pro
            100                 105                 110
Cys Gly Lys Thr Cys Arg Gly Asp Arg Asp Asp Glu Trp Met Gly Val
            115                 120                 125
Ser Leu Ala Arg Gln Pro Arg Ala Asp Gly Arg Val Leu Ala Cys Ala
            130                 135                 140
His Arg Trp Lys Asn Ile Tyr Tyr Glu Ala Asp His Ile Leu Pro His
145                 150                 155                 160
Gly Phe Cys Tyr Leu Ile Pro Ser Asn Leu Gln Ala Lys Gly Lys Val
            165                 170                 175
Leu Ile Pro Cys Tyr Glu Glu Tyr Lys Lys Tyr Gly Glu Glu His
            180                 185                 190
Gly Ser Cys Gln Ala Gly Ile Ala Gly Phe Phe Thr Glu Glu Leu Val
            195                 200                 205
Val Met Gly Ala Pro Gly Ser Phe Tyr Trp Ala Gly Thr Leu Lys Val
            210                 215                 220
Leu Asn Leu Thr Asp Asn Thr Tyr Phe Lys Leu Asn Asp Glu Ala Ile
225                 230                 235                 240
Met Asn Arg Arg Tyr Thr Tyr Leu Gly Tyr Ala Val Thr Ala Gly His
            245                 250                 255
Phe Ser His Pro Ser Ile Thr Asp Val Val Gly Gly Ala Pro Gln Asp
            260                 265                 270
Glu Gly Ile Gly Lys Val Tyr Ile Phe Arg Ala Asp Arg Arg Ser Gly
            275                 280                 285
Thr Leu Ile Lys Ile Phe Gln Ala Ser Gly Lys Lys Met Gly Ser Tyr
            290                 295                 300
Phe Gly Ser Ser Leu Cys Ala Val Asp Leu Asn Met Asp Gly Leu Ser
305                 310                 315                 320
Asp Leu Leu Val Gly Ala Pro Met Phe Ser Glu Ile Arg Asp Glu Gly
            325                 330                 335
Gln Val Thr Val Tyr Leu Asn Gln Gly His Gly Ala Leu Glu Glu Gln
            340                 345                 350
Leu Thr Leu Thr Gly Asp Ala Ala Tyr Asn Ala His Phe Gly Glu Ser
            355                 360                 365
Ile Ala Asn Leu Gly Asp Ile Asp Asp Asp Gly Phe Pro Asp Val Ala
            370                 375                 380
Val Gly Ala Pro Lys Glu Glu Asp Phe Ala Gly Ala Val Tyr Ile Tyr
385                 390                 395                 400
His Gly Asp Ala Asn Gly Ile Val Pro Lys Tyr Ser Met Lys Leu Ser
            405                 410                 415
Gly Arg Arg Leu Asn Pro Thr Leu Arg Met Phe Gly Gln Ser Ile Ser
            420                 425                 430
Gly Gly Ile Asp Met Asp Gly Asn Gly Tyr Pro Asp Val Thr Ile Gly
            435                 440                 445
Ala Phe Leu Ser Asp Ser Val Val Leu Arg Ala Arg Pro Val Ile
            450                 455                 460
Thr Val Asp Val Ser Ile Phe Leu Pro Gly Ser Ile Asn Ile Thr Ala
465                 470                 475                 480
Pro Gln Cys His Asp Gly Gln Gln Pro Val Asn Cys Leu Asn Val Thr
            485                 490                 495
Val Cys Phe Arg Phe His Gly Lys Asn Val Pro Gly Glu Ile Gly Leu
            500                 505                 510
Asn Tyr Asn Leu Thr Ala Asp Val Ala Gln Lys Glu Lys Gly Gln Leu
```

-continued

```
            515                 520                 525
Pro Arg Val Tyr Phe Val Leu Phe Gly Glu Thr Ala Gly Gln Val Ser
        530                 535                 540
Glu Arg Leu Gln Leu Ser His Met Asp Glu Val Cys His His Tyr Val
545                 550                 555                 560
Ala His Val Lys Arg Val Gln Asp Val Ile Ser Pro Ile Val Phe
                565                 570                 575
Glu Ala Ala Tyr Ser Leu Asp Glu His Val Met Gly Glu Glu Asp Arg
            580                 585                 590
Glu Leu Pro Asp Leu Thr Pro Val Leu Arg Trp Lys Lys Gly Gln Arg
        595                 600                 605
Ile Ser Gln Lys Asn Gln Thr Val Phe Glu Arg Asn Cys Gln Ser Glu
    610                 615                 620
Asp Cys Ala Ala Asp Leu Gln Leu Arg Gly Lys Leu Leu Leu Ser Ser
625                 630                 635                 640
Val Asp Glu Lys Thr Pro His Leu Ala Leu Gly Ala Val Lys Asn Ile
                645                 650                 655
Ser Leu Asn Ile Ser Ile Ser Asn Leu Gly Asp Asp Ala Tyr Asp Ala
            660                 665                 670
Asn Val Ser Phe Asn Val Ser Arg Glu Leu Phe Phe Ile Asn Met Trp
        675                 680                 685
Gln Lys Glu Glu Met Gly Ile Ser Cys Glu Leu Leu Glu Ser Asp Phe
    690                 695                 700
Leu Lys Cys Ser Val Gly Phe Pro Phe Met Arg Ser Lys Ser Lys Tyr
705                 710                 715                 720
Glu Phe Ser Val Ile Phe Asp Thr Ser His Leu Ser Gly Glu Glu Glu
                725                 730                 735
Ile Leu Ser Phe Ile Val Thr Ala Gln Ser Gly Asn Leu Glu Arg Ser
            740                 745                 750
Glu Ala Leu His Asp Asn Thr Leu Thr Leu Thr Val Pro Leu Val His
        755                 760                 765
Glu Val Asp Thr Ser Ile Thr Gly Ile Val Ser Pro Thr Ser Phe Val
    770                 775                 780
Tyr Gly Glu Ser Val Asp Ala Ser Asn Phe Ile Gln Leu Asp Asp Gln
785                 790                 795                 800
Glu Cys His Phe Gln Pro Val Asn Ile Thr Leu Gln Val Tyr Asn Met
                805                 810                 815
Gly Pro Ser Thr Leu Pro Gly Ser Ser Val Ser Ile Ser Phe Pro Ser
            820                 825                 830
Arg Leu Ser Pro Gly Gly Ala Glu Met Phe Gln Val Gln Asp Met Val
        835                 840                 845
Val Ser Gln Glu Lys Gly Asn Cys Ser Leu Gln Arg Asn Pro Thr Pro
    850                 855                 860
Cys Ile Ile Pro Gln Glu Gln Glu Asn Ile Phe His Thr Ile Phe Ala
865                 870                 875                 880
Phe Phe Ser Lys Ser Gly Arg Lys Val Leu Asp Cys Glu Lys Pro Gly
                885                 890                 895
Ser Phe Cys Leu Thr Leu His Cys Asn Leu Ser Ala Leu Pro Lys Glu
            900                 905                 910
Glu Ser Arg Thr Ile Asn Leu Tyr Met Leu Leu Asn Thr Glu Ile Leu
        915                 920                 925
Lys Lys Asp Ser Ser Val Ile Gln Phe Met Ala Arg Ala Lys Val
    930                 935                 940
```

Lys Val Glu Pro Ala Leu Arg Val Val Glu Ile Ala Asn Gly Asn Pro
945                 950                 955                 960

Glu Glu Thr Leu Val Val Phe Glu Ala Leu His Asn Leu Glu Pro Arg
                965                 970                 975

Gly Tyr Val Val Gly Trp Ile Ile Ala Ile Ser Leu Leu Val Gly Ile
            980                 985                 990

Leu Ile Phe Leu Leu Leu Ala Val  Leu Leu Trp Lys Met  Gly Phe Phe
        995                 1000                1005

Arg Arg  Arg Tyr Lys Glu Ile  Ile Glu Ala Glu Lys  Asn Arg Lys
    1010                1015                1020

Glu Asn  Glu Asp Gly Trp Asp  Trp Val Gln Lys Asn  Gln
    1025                1030                1035

<210> SEQ ID NO 3
<211> LENGTH: 36
<212> TYPE: DNA
<213> ORGANISM: Artificial
<220> FEATURE:
<223> OTHER INFORMATION: Primer

<400> SEQUENCE: 3
cgtggatccg agcgcatggc tgcggaagcg aggtgc                           36

<210> SEQ ID NO 4
<211> LENGTH: 36
<212> TYPE: DNA
<213> ORGANISM: Artificial
<220> FEATURE:
<223> OTHER INFORMATION: Primer

<400> SEQUENCE: 4
cagctcgagt cagtcatcat tgcttttgct gttgac                           36

<210> SEQ ID NO 5
<211> LENGTH: 36
<212> TYPE: DNA
<213> ORGANISM: Artificial
<220> FEATURE:
<223> OTHER INFORMATION: Primer

<400> SEQUENCE: 5
gtcaagcttc tggggatggg cggcccggct gggctg                           36

<210> SEQ ID NO 6
<211> LENGTH: 36
<212> TYPE: DNA
<213> ORGANISM: Artificial
<220> FEATURE:
<223> OTHER INFORMATION: Primer

<400> SEQUENCE: 6
cggtctagac acggtgggtc actggttttt ctggac                           36

<210> SEQ ID NO 7
<211> LENGTH: 4941
<212> TYPE: DNA
<213> ORGANISM: Mus musculus

<400> SEQUENCE: 7
cgggcccggg accgctcctt ccgagagcgc agacctctcg gcgggcatcg agaggacgcg    60
gggcgctggc ggccgtccct ggccttgctc cggctctcga ctgtagccca tcgccgcgtc   120

```
ccgggcttag actcgtgagc gtacggctcc cgccccgggc agcggcgtgt cccgggagcc    180
ccgatctgcg gggcagggcg cagggcggct ggccggctgg ggatgggcgg cccggctgcg    240
gcgcggaccg gcgccggagg gctccgcgcg ctgctgctgg cgctggtggc cgcggggtc     300
ccggccggcg cctacaacct ggacgcgcag cgcccggtac gcttccaggg ccctcaggc     360
tccttcttcg gctacgcggt gctggagcac ttccacgaca cacgcgctg ggtcctcgtg     420
ggtgcaccga aggcagattc taaatatagc acttcagtaa agtctcctgg agctgtgttt    480
aagtgtcgtg tccataccaa ccctgaccgg agatgcaccg agctggacat ggctcgaggg    540
aggactcgtg gtgcgccctg tgggaagacc tgcaggggag accgggatga cgagtggatg    600
ggggtgagcc tggcccggca gcccagagca gatggccgtg ttttggcctg tgcccatcgt    660
tggaaaaaca tctactacga agcagaccac atcctgcccc atggattctg ctacctcatc    720
ccttccaacc tccaggccaa aggcaaggtg ctgattccct gctacgaaga gtataagaag    780
aagtatgggg aagaacatgg ctcctgccag gccggaatag caggcttctt cacagaggaa    840
ctggtggtca tgggtgcccc aggctcgttt tattgggctg ggacactcaa ggtgctgaac    900
ctcacggaca cacatatttt taagttgaac gatgaagcga ttatgaacag acggtatact    960
tatctgggct atgcagtgac ggctggccac ttctctcatc catccatcac tgatgtggta   1020
gggggtgccc cacaggatga aggcattgga aaggtttata tatttagagc tgaccgaaga   1080
tcagggacct aataaagat cttttcaggca tcaggaaaaa agatgggctc ttacttcggc   1140
tcctccttgt gtgcagtcga cctgaacatg gacggcctct ctgacttgct cgtgggggct   1200
cccatgtttt ctgagatcag agatgagggg caggtcaccg tctacctcaa ccaaggacat   1260
ggagccctcg aggaacagct gaccctgact ggagatgccg cctacaacgc gcactttggg   1320
gagagcatcg ccaacctggg cgacattgat gatgacgggt tcccagatgt ggctgtcggg   1380
gcacctaagg aggaggactt tgctggcgca gtctacatct atcatggtga tgccaatggg   1440
attgtcccca gtactcaat gaagctgtct gggaggaggc taaacccgac cctgcggatg   1500
tttgggcagt ccatatcagg gggcattgat atggatggaa atggctatcc tgatgtcacc   1560
atcggagcct tcctgtccga cagcgtggtt ctcctcaggg ccagaccggt catcacggtg   1620
gatgtctcca tcttcctgcc aggctccatc aacatcacag cacctcagtg tcacgatgga   1680
caacagcctg tgaactgcct gaatgtcacc gtgtgcttcc ggttccatgg caagaatgta   1740
ccaggagaaa tcggtctgaa ctacaatctg acggctgatg tggcacagaa ggagaagggc   1800
cagctgccca gagtctattt tgtgttgttt ggagagacgg cagggcaggt ctcagaaagg   1860
ctgcagctgt cccacatgga cgaagtgtgt catcactacg tggcccacgt caagcggaga   1920
gtccaggatg tcatcagccc cattgtgttt gaagccgcct acagcctgga tgagcatgtg   1980
atgggtgagg aagaccggga gctgccagac ctgacaccag tgcttcgctg gaagaaggga   2040
caaaggatct cccagaagaa tcagacagtt tttgaaagga attgccaatc tgaggactgt   2100
gctgccgacc tgcagcttcg ggggaaactc ctgctttcca gtgttgacga gaaaaccccca  2160
cacctggctt tgggggctgt gaaaaatatc tctctaaaca tctccatctc caaccttgga   2220
gacgacgcct atgatgccaa cgtgtcccttt aatgtctcca gggaacttct tcttcatcaa   2280
catgtggcag aaggaggaga tgggcatttc ctgtgagctg ctggaatcag acttcctcaa   2340
gtgcagtgtg ggatttcctt tcatgaggtc aaagtctaag tatgaattca gtgtcatctt   2400
tgatacaagc cacctgtctg gggaagagga aattctcagc ttcatcgtga ctgctcagag   2460
tggcaacttg gagcgctctg aagccctaca tgacaacact ctcacactga cagtgcccct   2520
```

-continued

```
ggtgcatgaa gtggacacgt ccatcactgg aattgtgtcc caacctcct tcgtgtatgg      2580 cgagtctgtg gacgcatcca acttcattca gctggatgac caggagtgtc atttccaacc    2640
agtcaacatt actctccagg tctacaacat gggtcccagc acccttcctg ggtcatctgt    2700
cagcatctcc ttccccagcc ggctgtcacc tggtggcgca gagatgtttc aggtccagga    2760
catggtggta agccaagaga agggtaactg ctctctacaa agaaacccga cccctgcat     2820 catccctcaa gaacaagaga acatcttcca caccatattt gctttcttct ccaagtctgg    2880
aagaaaagtg ttggactgtg aaaagccagg agcttctgc ctaacgttgc actgcaacct     2940
tagtgctctt ccgaaagagg agagccgcac catcaaccta tacatgctac tgaacacaga    3000
gatactgaag aaggacagct cctctgtcat ccagttcatg gctcgagcca aggtgaaggt    3060
ggagcctgcc ctgagagtgg tggagatagc taacgggaac ccagaagaga ctctggtggt    3120
cttcgaggcc ttgcacaatc tggaaccccg tggctacgtt gtggggtgga tcatcgccat    3180
cagtttgctg gtggggatcc tcatttttct gctgctggct gtgctcctgt ggaagatggg    3240
cttcttccgc agaaggtaca agagatcat tgaagctgag aaaaaccgga agagaatga     3300 agatggttgg gactgggtcc agaaaaacca gtgacccacc gtgccagtca tgtgatgccc    3360
tcatgtcccc atcaccagcc tgtggtcctt gatctttgta tctttcatat ttggaagaaa    3420
gaaatcttct ccagattttt cggaggcccc actgatgctg ttctcttcct catcccgtca    3480
agcccggtgc cgacctgaga tggccacccc tccagccagg tcacatgact ggggccacca    3540
ccactcccct tctcaagatg aacttagaac tttggaaagg caagctacag agcaaagcaa    3600
tatttatgga tgcaacattg cgtggtcaac cctcagggga aaactgttac ctaaaagtat    3660
tttttataaa tgtaagcctt ttatattgat catgtctta tattgtatc aatgttttat      3720 tatttctatt aaatagttct ataattcact caagcactga atcttggaa atacatgtcc     3780 ctgcatacaa attttaaaag agaaggaact tattctactt tggaacttgt tgttagggaa    3840
gaaaaaaaaa acttgcagat aaaacaaact gaagaaacct catgaaatga atccaccaag    3900
ctggaggcac tgggaaagca caaggacat ggcaggccg cctaagacat ttattcccca      3960
ttgttaccac ccggagttaa gttcagagag cttgaagtat cggtgttttc tcttatggac    4020
ctctcactgg gagattctca gcaggaactg ggatggaaag cttggtttcc tctcagcagt    4080
tgctctgtac cacactgata catgcagcag gcactaaacc ctcttctgga gtcagcaagt    4140
gctggatgga caactggtca acctcagaat agcatctcat cctaaacaac atgtgtcaga    4200
gttcagagcc caggaccgaa gctgtgctct ctcagcaaag gcctgttttc tctgtgtgta    4260
agctgttacc ttgtggtata atgttaacac aagactctcc atttcctctg tcactcttgc    4320
tgtccccaac tggtggtgct gcagatacct ccccagagag gatcacccca catggtttgt    4380
gtttatgtct taggtggaat tctcaagagt cgaaccctga ataggactt gggtgtaaat     4440 aatttattga ggaagtcttc ccagaaggta acagtgagga agttgagaat acaagacagg    4500
agagtacagg gagccaggca acagtgtcct ttcagggac aacccacgag gtggcttcaa     4560
accagttgga tctaatgagc aagtcagact caggaacctg gacttttgtg atgccacgcc    4620 tgcagggat ataaactttc tgcccttagg tcttgctgac aagatgactc tgtcctctag     4680
aggagaactt tgggggcac cctcaagtaa ggagatccac aaatcatgca agaactctg      4740 agccaagagc tttagtgctc ccctccccca cacaagtgaa tgctaccttc agctttgtgt    4800
agccaaaaaa gccatgagtc taagctggtc ctaggagtca acattacat ctgacccatg     4860
```

```
accaagtcaa actcactaca aggaaggggc agccccccca aaaaaaaaaa acagtgcaca    4920
cccagctctt ttaagtttat c                                              4941

<210> SEQ ID NO 8
<211> LENGTH: 7272
<212> TYPE: DNA
<213> ORGANISM: Mus musculus

<400> SEQUENCE: 8
ctccaccaag agcgcatggc tgcggaagcg aggtgcagac cgaggtcccg agggatcgcc      60
ctccgggaag cggtgatgct gttgttgtac ttcggggtgc aaccgggca ctcctacaac     120 ctggacccgg agaatgcact gctgtaccag ggccctccg gcacgctgtt tggctactcg     180
gtggtgctgc acagccacgg tcgaagcgc tggctcatcg tgggggctcc cactgccagc     240
tggctctcta atgcctcagt ggtcaatcct ggggcgattt acagatgcgg gatcagaaag     300
aatccaaacc agacctgcga acagctccag ctgggtagcc ccagtggaga gccttgtggg     360
aagacatgcc tggaggagag ggataaccag tggctggggg tcacccttc cagacagcct     420 ggagaaaatg gctctatcgt gacttgtggg cacaggtgga aaaatatttt ttacatgaag     480
agcgataaca aactccccac tggcatttgc tacgtcatgc cttctgattt gcggacagaa     540
ctgagtaaaa ggatggcccc gtgttacaaa gattatacga gaaaatttgg agaaaatttt     600
gcatcatgtc aagctggaat atctagtttt tacacacagg atttaattgt gatggggcc     660 ccgggatcat cgtactggac tggcaccgtc tttgtctaca atataactac aaaccaatac     720
aaagcatttg tagacagaca gaaccaagta aaatttggaa gctacttagg ctactcagtt     780
ggagctggac attttcgaag tccacatact accgaagtcg tgggaggagc ccctcaacac     840
gaacagatag gaaaagcata tatttagc attgatgaaa acgaactgaa catcgtatat     900
gaaatgaaag gtaaaaagct tggctcatac tttggagctt ctgtctgcgc tgtggacctc     960
aatgcagatg gcttctcaga tctccttgtt ggagctccca tgcagagcac catcagggag    1020
gaaggaagag tattcgtgta catcaactct ggcatgggag ctgtgatggt tgaaatggaa    1080
agggtccttg tcggaagtga caaatatgct gcaagatttg gggagtctat agcgaatctt    1140
ggcgacattg acaatgacgg ctttgaagat attgctattg gtgcaccaca agaagacgac    1200
ttgcgaggtg ctgtctacat ttacaatggc cgagtcgatg aatctcctc cacctactca    1260 cagagaattg aaggacagca aatcagcaaa tcattaagga tgtttggaca atctatctca    1320
ggacaaattg atgcagacaa caatggatat gttgatgtag ccattggtgc atttcactct    1380
gattctgcag tgttgctaag gacaaggcct gtagtgattg ttgaagcatc tttaagccat    1440
cctgagtctg taaataggac aaagtttgac tgtactgaaa atggacttcc atctgtgtgc    1500
atgcatctta cactgtgttt ctcatataaa ggcaaagagg tcccaggcta catcgttttg    1560
ttttacaatg tgagcttgga tgtgcacagg aaggcagagt ctccgtcaag atttattttc    1620
ttctctaatg ggacttctga cgtgattaca ggaagcatac gagtttcaag cagtggagag    1680
aaatgtagga cacaccaggc attcatgcgg aaagatgtgc gagacatcct tacccccatt    1740
catgtagagg ccacatacca ccttgggcat catgtgatca ccaaacgaaa cactgaggaa    1800
tttccaccac tccagccgat ccttcagcag aagaagaaa aagacgttat tagaaaaatg    1860
ataaactttg caaggttttg tgcctatgaa aattgctctg ctgatctcca gtttctgca    1920 aaagttggat ttttgaagcc atatgaaaat aaaacctatc ttgctgttgg agcatgaag    1980 accataatgc taaacgtgtc cttgttcaac gctggcgatg atgcttacga aaccactctg    2040
```

```
aatgtccaac tccccacagg cctttatttc attaagatct tagacctgga agagaaacaa    2100
ataaactgcg aagtgactga gagctcaggc atagtgaagc ttgcctgcag cctaggttac    2160
atatatgtgt atcgcctctc aaggatagac attagctttc tcctggatgt gagctcactc    2220
agcagggcac atgaggacct cagcatcagt gtgcatgcct cctgtgaaaa cgagggtgaa    2280
ttggaccaag tgagggacaa cagagtaacc ttaacgatac ctctaaggta tgaggttatg    2340
ctgactgttc atgggcttgt gaacccaact tcatttgtgt atggatctag cgaagaaaac    2400
gagccagaaa catgcatggc cgagaagctg aacctcactt tccatgttat aaacactggg    2460
attagcatgg ctccaaatgt tagtgtgaaa ataatggtac caaattcttt tctccctcaa    2520
gatgataagt tgttcaacgt tttggatgtc cagacaacta cagggcaatg ccatttaaa     2580 cactatggaa gagagtgtac atttgcacag caaaaaggca tagcggggac gttgaccgat    2640
atagtcaaat tcctatcaaa gactgataag agactcctgt attgcatgaa agctgatcaa    2700
cactgtttag atttcttatg caatttcgga aaaatggaaa gtgggaagga agccagcgtt    2760
catattcagc tggagggcag gccatccatc ttggaaatgg atgagacctc atcactcaag    2820
tttgaaataa aagcaacagc ttttccagag ccacacccaa aagttattga actaaataaa    2880
gatgagaacg tggcccatgt tttcttggaa ggctccatc atcaaagacc caaacgacat     2940
ttcaccatca ttattattac catcagcttg ctacttggac ttattgtact tttattaatt    3000
tcatgtgtta tgtggaaggc tggattcttt aaaagacagt acaaatctat cctacaagaa    3060
gaaaacagga gagacagctg gagttatgtc aacagcaaaa gcaatgatga ctgaagactt    3120
ctacactgag agaactgaaa aactcaggtt aggaaaaaga aatcctgttc agaagacccg    3180
tcagaatttc ttcttttttt ccatgtgctt atgattttgt gacatactct tagtgcaggg    3240
gaaatcttca agaagaagc tacccaaagg tggcttgtca gcttcggtgg atgagtgaag     3300
caaaacacta agctctgga tgtaccggag aggtgacctg tttaagacaa cttaaagcta     3360
gagagaatcc agactcagca gggccgactt aaagggaatg attttttcaac atcactgatg    3420 aagtggctca tctcagtgaa atggatgcca tgatgtggaa acttgttggc ttcaaatact    3480
tttatcttca aactatgatc atgatctttg aattcactga gactctttca aatggctgtt    3540
ccaagattgt ctaatggata agtcattttt tattagatat tttctttatt tacatttcaa    3600
atgttatccc ctttcctagt ttccactcca aaatcccct atcctctccc ctgtcccctg     3660
ctccccaatc gacccactcc cgcttcctgg ccaaggcgtt ccctatact ggggaataga     3720 accttcacag gaccaagggc ctctcctcct attgacagag cacagggtcc ccaatgaagg    3780
agttagagaa ataccccaag gagctgaagg ggtttgcagc cccataggag gaacaacaat    3840
atgaactaac cagtaacccc agagctcctt gggactaaac caccaaccaa agaaaacaca    3900
cggagagacg catggctcta gctggatcaa tcattttaaa gcagaggacc tgaagactgc    3960
tcttggtggt gctgcatccc tgggctgtgt ccctacagcc ctttactct gcagatagga    4020 actgtaaaat cctaaagaac aaaatccgtt tgcagcagga tggcttctgg ggaaatggtc    4080
agctgcggac tcttgtgtgt atgtacatat acttttttaa aggataaaaa tctcaatcta    4140
cttctttatt aagaacaccc aggaatagtt tgcatcttct aagcttcacc tttaatacca    4200
attcttaaga attttatcct catagcagat tataaatatc gcactttagc tgatacacac    4260
tgatacaaca tgaactgcag ctcactgatg atcgaaaatt gtgtgaagag agatttagga    4320
accaatattt cataaaacat tcactgcatc aaattatgca aacatgagta tctgctagga    4380
```

```
tattgttgtt tctcttggtc tggttgaata tacataaact aggactctaa aacaccacat    4440
tctgtcatag aaatggagac acaaaaatca tagttggaac tgcaaatcac tgatcaagtt    4500
tgtgtgcagt ggcatcaaaa ttcccatgcg ataatgcatg cttgatgttg ttgaacaaga    4560
tactatttta aaatgaaata gcttctacct gggtttcaca taatttgtct gtaattacaa    4620 tcattttgt agtatttatt tcatatatgt agtttgataa atgtaagttt tcatttgaat     4680
ctgttatgtg taagcaagct aaggccagac tttgaacatg tgctgggtaa aaggggcagc    4740
cttcagtgtt gtgaagaaag atcgctttac aggaagggtt tgatgccagc tggcccttcc    4800
tcagatttcc tgacttgtga ggatggcttg ttcacaagcc tctggctgga gccgtggagg    4860
gaggttttga gtgctgaaac ttgagcatag agcatcagat ctgggtgagc agaaaccata    4920
tttaattaga tgcttatatt tttaagggat gctttttgt gtaaaaggtt taagttgatg     4980
gttttcttat aaaaattcaa gtagttattt catgaggatg ccaaagttaa tagatgagaa    5040
atcaatatca ttttagacct accgtttcaa ggaatggtct ctgaggagag ttaaatgtgg    5100
atcattgcac tgaaaaccga ctcctgcctt tcaggtacaa agaacgtag ctacctcctg     5160 ggccacattt tgcccaatta gaaagaaata ttttatatt tattaataaa acttagaatt     5220
ttatataagc tttaaaatgt agttatttca aaagatgctg ttatgggatg ggtagtagaa    5280
tagtagccta agaggaagaa atgttttta agtgggtgtt cgtggttatg ttactatctc     5340
actgtgaagt ctgagatttt acagaagttt tgttttacta ggttacagga gatactaaag    5400
aattatcttc aacagtattg agagagcaca atgttgttaa aattagatct aacaaacacc    5460
ttccaaaaat caaaactttg attttttca ttaatttcat attttttgat tttcaaatac      5520
ctggctacta ttttaattat attaaaatat tttaattgca ttaaagtaga tactttaatt    5580
atattaaata gatagcttca ttaaaatgtg ttgcagtaaa tctctccaac ccaaatatgc    5640
cttggcaatg aaaacacaac acagttaata tgattgcatg ctgtgcgcct agattgggca    5700
gatctactgc tacactactg tcttccacag cttatgagac cccttagaac ttgcggtttc    5760
tccaggccat gtgcttctgc tctgcttcac ttcatcttcc tccccctctg catcctctcc    5820
ctcttccatt ttctccttct tttctctccc taccttcggc tccgccttcc cttttatctg    5880
cccaatcatc agctctcctt tattttacaa attaaggtgg gaatcaggtt tacaggaaat    5940
cacctgagtg ctgactcatt ccttgttcac aaccgctcat gggagaacag aattaacatc    6000
aaatataatt agccccaggg ctatcctcaa catttacccc cttctgtcca attaaaagac    6060
tattttatct cagatataat tgaacataac aattattatt ttgtaattta taagtacag     6120 gagacctaac acccagtcca tcatctttgt taattaaata aaaatctctg tcatctatcc    6180
ttacttaaaa gactatagtt ctgcacctgg ctagttctgc atctgaaaac catcctctca    6240
aatctattcc tctcaaagtg aaaagcctgg gctcgcctga gactatgtag ttttcaacc     6300 tcaacataaa tccaagaatg actgatatta actgaaaata tataggaagc ctaacatagc    6360
ttccaaaatt tagataattt gttgagacca ctggtcactt ggacagtccc ttacttcaac    6420
agggtggagc tttgatcttc aggctactgg ccttagtcat ctgacaagac ttagagaaac    6480
aagaatatta aggactagcc tactgtctcg gcagaatcaa gctgtcctaa cctgtagttg    6540
tgtcctttct ttgacagta ctatatctgt agatgaaatg agccaattct tgcctagtga     6600
ctttcaccac aactagagta actcaaagat gctcagtttc ttctttgaat ccaagacagg    6660
gaaagctgtc aggagcagac tagtctcaac aacaagtgaa taaataacat caaacttcac    6720
attctgtgga cttctgatgt ttttggaaaa ccaattatct atatgaagta atctgaactg    6780
```

```
ttctctgaac ctctctcagc catttctgat taaaataact gaaaacaccc taacaataaa      6840
ctcagagcca agaatttcct atctgaccct taactcacag gcttaaacat ctcagctctg      6900
tttatcataa cagcaattga aggactgggt ctaagccttg tacttcaaaa tttttagtat      6960
caaagacaac ctataataac cacccgcagc cgcaaagctt agggaactgg gatgatgaat      7020
cttcataact tcttcaagct gatatgggcg ttgagatatt tttgaaggaa ggggaagaa      7080 tagggaaagg gggagttagt tggccttagg aaggccccac catgattgta ttagtttctg      7140
atgtctctgt cctgactgga tccggatgaa aaaccaagat atcagttcag gcaagtcagt      7200
tcagcatgtc tgatgatgaa attcaccaag gctgtatatt ctgtaatata taaatctcaa      7260
aaaaaaaaaa aa                                                          7272

<210> SEQ ID NO 9
<211> LENGTH: 3588
<212> TYPE: DNA
<213> ORGANISM: Homo sapiens

<400> SEQUENCE: 9
ccgcgctcgg cgccctgctc gccgggcaga gggaaggcg gccggctggg gatgggcggc         60
ccggctgcgc cgaggggcgc cgggaggctc cgcgcgctgc tgctggcgct ggtggtcgcg       120
gggatccccg cgggcgccta caacctcgac ccgcagcgcc ccgtgcactt ccagggcccc       180
gctgactcgt tcttcggcta cgcagttctg gagcatttcc acgacaacac gcgctgggtc       240
cttgtgggcg caccaaaggc agattccaaa tacagccctt cagtgaagtc tcctgggct       300 gtgtttaagt gccgtgttca caccaaccct gaccggagat gcaccgaact ggacatggct       360
cgagggaaga tcggggcac gtcctgcgga aagacctgcc gggaagaccg cgatgatgag       420
tggatggggg tgagcctggc ccgacagccc aaggctgatg ccgtgtgtt ggcctgtgct       480 catcgctgga agaacatcta ctatgaagcc gaccacatcc tacccatgg cttctgctac      540 atcatcccct ccaacctcca ggccaaaggc aggacactga tcccttgcta tgaagagtat       600
aagaagaagt acggagagga acacggctcc tgccaggctg ggtatagcgg gcttcttcact      660 gaggagctgg tggtgatggg tgctccaggg tcatttttatt gggctggaac catcaaagtg      720
ctgaacctta cggacaacac ctatttaaaa ctgaacgacg aagtgatcat gaacaggcgg       780
tacacctacc tgggctacgc agtgaccgct ggccacttct ctcacccgtc caccattgat       840
gtggtaggag gtgcccccaca ggacaaaggc atcggcaagg tttatatttt cagagctgac       900
cgaagatcag gcaccttaat taagatcttt caagcatcag gtaaaaagat gggctcttac       960
ttcggctcct ccttgtgcgc agttgacctg aatgggacg cctctctga cctgctggtg      1020 ggggccccca tgttttctga atcagggat gagggacagg tcactgtcta catcaacaga      1080
ggaaatggag ccctcgagga gcagctggct ctgactgggg atggtgccta caatgcgcac      1140
tttggagaga gcattgccag cctggacgat ctggacaatg atgggttccc agatgtggcc      1200
attggtgcac caaggagga tgacttcgca ggggcggtct atatctatca tggtgatgcc      1260
ggtgggatag tccctcagta ctcaatgaaa ctgtctgggc agaagataaa tccagtgctc      1320
cggatgtttg gtcagtccat atcggaggc attgatatgg atgaaatgg ctatcctgat      1380 gtcactgttg gagccttcat gtccgacagc gtggttcttc tcagagcaag gcctgtcatt      1440
acggtggatg tctccatctt cctcccgggc tccatcaaca tcacagcgcc tcagtgtcac      1500 gacgacagc agcctgtgaa ctgcctgaac gtcaccacct gcttcagctt ccatggcaaa      1560
```

```
cacgttccag aagagattgg cctgaattat gttctgatgg ctgacgtggc caaaaaggag    1620
aagggccaga tgcccagggt ctactttgtg ctgctgggag agaccatggg tcaggtcaca    1680
gagaagctgc agctgactta catggaggag acgtgtcgtc actatgtggc ccatgtgaag    1740
cggagggtgc aggacgtcat cagcccgatc gtgtttgaag cagcctacag cctcagtgag    1800
catgtgactg agaggagga gagggaactg ccgcctctga caccagttct ccgctggaaa    1860
aagggacaaa agattgccca aaagaatcag actgtttttg aaaggaattg ccgttcagag    1920
gactgtgccg cagacctgca gcttcagggt aaactgctgc tctccagtat ggatgagaaa    1980
accctgtatc tagctttggg ggctgtgaag aacatctccc taaacatctc tatctccaac    2040
ctcggagatg atgcctatga tgccaacgtg tccttcaatg tttcccggga gctcttcttc    2100
atcaacatgt ggcagaagga ggagatgggc atctcctgtg agctgctgga atcggacttc    2160
ctcaaatgca gcgtgggatt tcctttcatg aggtcaaagt caaagtatga attcagcgtg    2220
atctttgata caagccacct gtctggggaa gaggaagttc tcagcttcat tgttactgct    2280
cagagtggca acacggagcg ctctgaatcc ctgcatgaca cacctcgt gctgatggtg    2340 ccactgatgc acgaggtgga cacgtccatc accggaatca tgtctccaac ctcctttgta    2400
tatggcgagt ccgtggacgc agccaacttc attcagctgg atgacctgga gtgtcacttt    2460
cagcccatca atatcaccct tcaggtctac aacactggcc aagcaccct tccagggtca    2520 tctgtcagca tctctttccc taatcgactc tcatctggtg gtgcagagat gtttcatgtc    2580
caggaaatgg tggtgggcca agagaaggga aactgctctt tccagaaaaa cccaactccc    2640
tgcatcatcc ctcaagaaca agaaaatatc ttccacacaa tatttgcttt tttcacaaag    2700
tctggaagaa aagtcttgga ctgtgaaaaa ccaggaattt cttgcctaac agcacactgt    2760
aactttagtg ctcttgctaa agaagaaagt cgtactatag acatttacat gctgctgaac    2820
acagaaatac tgaaaaagga cagttcgtct gtcatccagt tcatgtcccg cgccaaggtg    2880
aaggtggatc ctgccctaag ggtggtggaa atagctcatg gaacccaga agaggtgacg    2940 gtggtcttcg aggccctgca caatctggag ccccgtggct acgtcgtggg gtggatcatc    3000
gccatcagtt tgttggtggg aatcctcatc ttcctgctgc tggccgtgct gctctggaag    3060
atgggcttct ttcgccgaag gtacaaagaa attatcgaag ctgagaagaa ccggaaagag    3120
aatgaagaca gttgggactg ggtccagaaa accagtgag ctgccacacc agtcacatga    3180
cctgatcact agcctgtcat ccttggtctt tgtatcttcc atatttgaa aaaaaaaatc    3240 ttctccagat ttttcggagg ccccactgat gctgttctct tcttcattct atcaagccca    3300
ggtgccagcc tgaggcagcc acttcggcca ggtcacacga ccgggggcag caccacttcg    3360
ctttaaagac tctgaacttt ggagagtgac agagccgagc aatatttagg atgcaacacg    3420
catggtcacc ctcagggaa aactgttaaa gtatttttat aaatataagc cttttatact    3480
gattattctt ttatatttgt atcgatatta tttctattaa atagttataa ttcactcaag    3540
cactgattct ggcctaaaat cttggaagtc catgaataca aatttttaa                3588
```

<210> SEQ ID NO 10
<211> LENGTH: 4932
<212> TYPE: DNA
<213> ORGANISM: Homo sapiens
<400> SEQUENCE: 10

```
ggcagggcac acctggattg cattagaatg agactcacta cccagttcag gtgtgttgcg      60
ttgtgggtct ccggcacatt tcagaggctg attaggaccc tgaccccaca ctgggggttta    120
```

-continued

| | | | | | |
|---|---|---|---|---|---|
| caccccctaaa | agcaggtgtg | tcccgtggca | actgagtggg | tgcgtgaaaa | ggggggatca | 180 |
| tcaattacca | gctggagcaa | tcgaatcggt | taaatgtgaa | tcaagtcaca | gtgcttcctt | 240 |
| aacccaacct | ctctgttggg | gtcagccaca | gcctaaaccg | cctgccgttc | agcctgagag | 300 |
| gctgctgcta | gcctgctcac | gcatgcagcc | cgggctgcag | aggaagtgtg | gggaggaagg | 360 |
| aagtgggtat | agaagggtgc | tgagatgtgg | gtcttgaaga | gaatagccat | aacgtctttg | 420 |
| tcactaaaat | gttccccagg | ggccttcggc | gagtcttttt | gtttggtttt | ttgttttttaa | 480 |
| tctgtggctc | ttgataattt | atctagtggt | tgcctacacc | tgaaaaacaa | gacacagtgt | 540 |
| ttaactatca | acgaaagaac | tggacggctc | cccgccgcag | tcccactccc | cgagtttgtg | 600 |
| gctggcattt | gggccacgcc | gggctgggcg | gctcacagcg | aggggcgcgc | agtttggggt | 660 |
| cacacagctc | cgcttctagg | ccccaaccac | cgttaaaagg | ggaagcccgt | gccccatcag | 720 |
| gtccgctctt | gctgagccca | gagccatccc | gcgctctgcg | ggctgggagg | cccgggccag | 780 |
| acgcgagtcc | tgcgcagccg | aggttcccca | gcgcccctg | cagccgcgcg | taggcagaga | 840 |
| cggagcccgg | ccctgcgcct | ccgcaccacg | cccgggaccc | cacccagcgg | cccgtacccg | 900 |
| gagaagcagc | gcgagcaccc | gaagctcccg | gctcggcggc | agaaaccggg | agtggggccg | 960 |
| ggcgagtgcg | cggcatccca | ggccggcccg | aacgtccgcc | cgcggtgggc | cgacttcccc | 1020 |
| tcctcttccc | tctctccttc | ctttagcccg | ctggcgccgg | acacgctgcg | cctcatctct | 1080 |
| tggggcgttc | ttccccgttg | gccaaccgtc | gcatcccgtg | caactttggg | gtagtggccg | 1140 |
| cttagtgttg | aatgttcccc | accgagagcg | catggcttgg | gaagcgaggc | gcgaacccgg | 1200 |
| gccccgaagc | cgccgtccgg | gagacggtga | tgctgttgct | gtgcctgggg | gtcccgaccg | 1260 |
| gccgccccta | caacgtggac | actgagagcg | cgctgcttta | ccagggcccc | cacaacacgc | 1320 |
| tgttcggcta | ctcggtcgtg | ctgcacagcc | acggggcgaa | ccgatggctc | ctagtgggtg | 1380 |
| cgcccactgc | caactggctc | gccaacgctt | cagtgatcaa | tcccggggcg | atttacagat | 1440 |
| gcaggatcgg | aaagaatccc | ggccagacgt | gcgaacagct | ccagctgggt | agccctaatg | 1500 |
| gagaaccttg | tggaaagact | tgtttggaag | agagagacaa | tcagtggttg | ggggtcacac | 1560 |
| tttccagaca | gccaggagaa | aatggatcca | tcgtgacttg | tgggcataga | tggaaaaata | 1620 |
| tattttacat | aaagaatgaa | aataagctcc | ccactggtgg | ttgctatgga | gtgcccctg | 1680 |
| atttacgaac | agaactgagt | aaaagaatag | ctccgtgtta | tcaagattat | gtgaaaaat | 1740 |
| ttggagaaaa | ttttgcatca | tgtcaagctg | gaatatccag | ttttacaca | aaggatttaa | 1800 |
| ttgtgatggg | ggccccagga | tcatcttact | ggactggctc | tcttttttgtc | tacaatataa | 1860 |
| ctacaaataa | atacaaggct | tttttagaca | aacaaaatca | agtaaaattt | ggaagttatt | 1920 |
| taggatattc | agtcggagct | ggtcattttc | ggagccagca | tactaccgaa | gtagtcggag | 1980 |
| gagctcctca | acatgagcag | attggtaagg | catatatatt | cagcattgat | gaaaagaac | 2040 |
| taaatatctt | acatgaaatg | aaaggtaaaa | agcttggatc | gtactttgga | gcttctgtct | 2100 |
| gtgctgtgga | cctcaatgca | gatggcttct | cagatctgct | cgtgggagca | cccatgcaga | 2160 |
| gcaccatcag | agaggaagga | agagtgtttg | tgtacatcaa | ctctggctcg | ggagcagtaa | 2220 |
| tgaatgcaat | ggaaacaaac | ctcgttggaa | gtgacaaata | tgctgcaaga | tttggggaat | 2280 |
| ctatagttaa | tcttggcgac | attgacaatg | atggctttga | agatgttgct | atcggagctc | 2340 |
| cacaagaaga | tgcttgcaa | ggtgctattt | atatttacaa | tggccgtgca | gatgggatct | 2400 |
| cgtcaacctt | ctcacagaga | attgaaggac | ttcagatcag | caaatcgtta | agtatgtttg | 2460 |

```
gacagtctat atcaggacaa attgatgcag ataataatgg ctatgtagat gtagcagttg   2520
gtgcttttcg gtctgattct gctgtcttgc taaggacaag acctgtagta attgttgacg   2580
cttctttaag ccaccctgag tcagtaaata gaacgaaatt tgactgtgtt gaaaatggat   2640
ggccttctgt gtgcatagat ctaacacttt gtttctcata taagggcaag gaagttccag   2700
gttacattgt tttgttttat aacatgagtt tggatgtgaa cagaaaggca gagtctccac   2760
caagattcta tttctcttct aatggaactt ctgacgtgat tacaggaagc atacaggtgt   2820
ccagcagaga agctaactgt agaacacatc aagcatttat gcggaaagat gtgcgggaca   2880
tcctcacccc aattcagatt gaagctgctt accaccttgg tcctcatgtc atcagtaaac   2940
gaagtacaga ggaattccca ccacttcagc caattcttca gcagaagaaa gaaaaagaca   3000
taatgaaaaa aacaataaac tttgcaaggt tttgtgccca tgaaaattgt tctgctgatt   3060
tacaggtttc tgcaaagatt gggtttttga agccccatga aaataaaaca tatcttgctg   3120
ttgggagtat gaagacattg atgttgaatg tgtccttgtt taatgctgga gatgatgcat   3180
atgaaacgac tctacatgtc aaactacccg tgggtcttta tttcattaag attttagagc   3240
tggaagagaa gcaaataaac tgtgaagtca cagataactc tggcgtggta caacttgact   3300
gcagtattgg ctatatatat gtagatcatc tctcaaggat agatattagc tttctcctgg   3360
atgtgagctc actcagcaga gcggaagagg acctcagtat cacagtgcat gctacctgtg   3420
aaaatgaaga ggaaatggac aatctaaagc acagcagagt gactgtagca ataccttaa    3480 aatatgaggt taagctgact gttcatgggt ttgtaaaccc aacttcattt gtgtatggat   3540
caaatgatga aaatgagcct gaaacgtgca tggtggagaa aatgaactta actttccatg   3600
ttatcaacac tggcaatagt atggctccca atgttagtgt ggaaataatg gtaccaaatt   3660
cttttagccc ccaaactgat aagctgttca acattttgga tgtccagact actactggag   3720
aatgccactt tgaaaattat caagagtgtg gtgcattaga gcagcaaaag agtgcaatgc   3780
agaccttgaa aggcatagtc cggttcttgt ccaagactga taagaggcta ttgtactgca   3840
taaaagctga tccacattgt ttaaatttct tgtgtaattt tgggaaaatg gaaagtggaa   3900
aagaagccag tgttcatatc caactggaag gccggccatc catttagaa atggatgaga    3960 cttcagcact caagtttgaa ataagagcaa caggttttcc agagccaaat ccaagagtaa   4020
ttgaactaaa caaggatgag aatgttgcgc atgttctact ggaaggacta catcatcaaa   4080
gacccaaacg ttatttcacc atagtgatta tttcaagtag cttgctactt ggacttattg   4140
tacttctgtt gatctcatat gttatgtgga aggctggctt ctttaaaaga caatacaaat   4200
ctatcctaca agaagaaaac agaagagaca gttggagtta tatcaacagt aaaagcaatg   4260
atgattaagg acttctttca aattgagaga atggaaaaca gactcaggtt gtagtaaaga   4320
aatttaaaag acactgttta caagaaaaaa tgaattttgt ttggacttct tttactcatg   4380
atcttgtgac atattatgtc ttcatgcaag gggaaaatct cagcaatgat tactctttga   4440
gatagaagaa ctgcaaaggt aataatacag ccaaagataa tctctcagct tttaaatggg   4500
tagagaaaca ctaaagcatt caatttattc aagaaaagta agcccttgaa gatatcttga   4560
aatgaaagta taactgagtt aaattatact ggagaagtct tagacttgaa atactactta   4620
ccatatgtgc ttgcctcagt aaaatgaacc ccactgggtg ggcagaggtt catttcaaat   4680
acatctttga tacttgttca aaatatgttc tttaaaaata taatttttta gagagctgtt   4740
cccaaatttt ctaacgagtg gaccattatc actttaaagc cctttattta taatacattt   4800
cctacgggct gtgttccaac aaccattttt tttcagcaga ctatgaatat tatagtatta   4860
```

-continued

```
taggccaaac tggcaaactt cagactgaac atgtacactg gtttgagctt agtgaaatga        4920
cttccggaat ct                                                           4932

<210> SEQ ID NO 11
<211> LENGTH: 36
<212> TYPE: DNA
<213> ORGANISM: Artificial
<220> FEATURE:
<223> OTHER INFORMATION: Primer

<400> SEQUENCE: 11
acgctcgagt gtaccatgtt ccccaccgag agcgca                                   36

<210> SEQ ID NO 12
<211> LENGTH: 30
<212> TYPE: DNA
<213> ORGANISM: Artificial
<220> FEATURE:
<223> OTHER INFORMATION: Primer

<400> SEQUENCE: 12
tcatctagat taatcatcat tgcttttact                                          30

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
tcgaagcttc tggggatggg cggcccggct                                          30

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
acctctagat cactggtttt tctggaccca                                          30

<210> SEQ ID NO 15
<211> LENGTH: 7
<212> TYPE: PRT
<213> ORGANISM: Homo sapiens

<400> SEQUENCE: 15

Ser Val Val Tyr Gly Leu Arg
                5

<210> SEQ ID NO 16
<211> LENGTH: 5
<212> TYPE: PRT
<213> ORGANISM: Homo sapiens

<400> SEQUENCE: 16

Gly Arg Gly Asp Ser
                5

<210> SEQ ID NO 17
<211> LENGTH: 8
<212> TYPE: PRT
```

```
<213> ORGANISM: Homo sapiens

<400> SEQUENCE: 17

Ala Glu Ile Asp Gly Ile Glu Leu
                 5
```